United States Patent [19]
Kohl et al.

[11] Patent Number: 6,107,312
[45] Date of Patent: *Aug. 22, 2000

[54] THIOPYRIDINES FOR USE IN THE CONTROL OF HELICOBACTER BACTERIA

[75] Inventors: Bernhard Kohl; Gerhard Grundler; Jörg Senn-Bilfinger, all of Constance, Germany

[73] Assignee: BYK Gulden Lomberg Chemische Fabrik GmbH, Constance, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/750,792
[22] PCT Filed: Jun. 9, 1995
[86] PCT No.: PCT/EP95/02236
  § 371 Date: Sep. 16, 1997
  § 102(e) Date: Sep. 16, 1997
[87] PCT Pub. No.: WO95/34553
  PCT Pub. Date: Dec. 21, 1995

[30] Foreign Application Priority Data

Jun. 10, 1994 [CH] Switzerland ............... 1846/94

[51] Int. Cl.[7] ............... A61K 31/4439; C07D 401/12
[52] U.S. Cl. ............... 514/338; 514/234.5; 514/241; 514/256; 514/303; 514/318; 544/124; 544/131; 544/215; 544/333; 546/118; 546/194; 546/256; 546/268.7; 546/269.1; 546/269.7; 546/270.7; 546/271.4; 546/272.4; 546/273.7
[58] Field of Search ............... 546/283.4, 280.4, 546/270.7, 269.7, 272.7, 274.7, 268.7, 273.7, 194; 544/124; 514/336, 338, 340, 341, 342, 234.5, 318

[56] References Cited

U.S. PATENT DOCUMENTS 4,873,337 10/1989 Sih et al. ............... 546/271
5,039,806 8/1991 Brandstram et al. ............... 546/271
5,504,082 4/1996 Kawakita et al. ............... 514/234.5

FOREIGN PATENT DOCUMENTS 150586 8/1985 European Pat. Off. .
0610049 4/1994 Japan .
93/24480 12/1993 WIPO .
94/13290 6/1994 WIPO .
94/19346 9/1994 WIPO .

OTHER PUBLICATIONS

Sih et al., "Studies on (H+–K+)–ATPase Inhibitors of Gastric Acid Secretion. Prodrugs of 2–[(2–Pyridinylmethyl)sulfinyl]benzimidazole Proton-Pump Inhibitors," J. Med. Chem, vol. 34, pp. 1049–1062, 1991.

Parsonnet et al., "Helicobacter Pylori Infection and The Risk of Gastric Carcinoma," The New England Journal of Medicine, vol. 325, No. 16, pp. 1127–1131, 1991.

Takeshii et al., "Benzimidazoles as bactericides," Chemical Abstracts, vol. 121, No. 11, Abstract No. 125211t, 1994.

Primary Examiner—Richard L. Raymond
Attorney, Agent, or Firm—Jacobson, Price, Holman & Stern, PLLC

[57] ABSTRACT

Thiopyridines of formula (I)

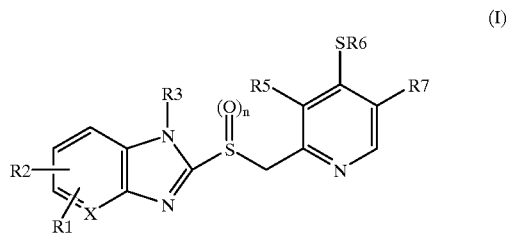

in which the substituents and symbols are as defined in the specification are suitable for use in controlling Helicobacter bacteria. They are compounded into medicament compositions and administered to subjects afflicted with a disease based on Helicobacter bacteria.

11 Claims, No Drawings

THIOPYRIDINES FOR USE IN THE CONTROL OF HELICOBACTER BACTERIA

This application is a 371 of PCT/EP95/02236, filed Jun. 9, 1995.

FIELD OF USE OF THE INVENTION

The invention relates to compounds which are to be used in the pharmaceuticals industry as active compounds for the preparation of medicaments.

KNOWN TECHNICAL BACKGROUND

European Patent Application 150 586 discloses 2-(pyridylmethylthio- and -sulfinyl)benzimidazoles which can be substituted in the 4-position in the pyridine part of the molecule, inter alia by alkylthio or arylthio radicals. A long-lasting inhibition of secretion of gastric acid is stated for the compounds described. International Patent Application WO89/03830 reports that these and other structurally similar compounds are said to be suitable for treatment of osteoporosis. International Patent Application WO92/12976 describes 2-(pyridylmethylthio- and -sulfinyl)-benzimidazoles which are substituted in a particular manner and are said to be active against Helicobacter bacteria, and for which it is furthermore disclosed that they are said to be suitable for prevention and treatment of a whole range of diseases of the stomach. International Patent Application WO93/24480 describes further 2-(pyridylmethylthio- and -sulfinyl)-benzimidazoles which are substituted in a particular manner and are said to be active against Helicobacter bacteria.

DESCRIPTION OF THE INVENTION

The invention relates to compounds of the formula I (see attached formula sheet I, in which R1 is hydrogen, 1–4C-alkyl, 1–4C-alkoxy or halogen, R2 is hydrogen, 1–4C-alkyl, 1–4C-alkoxy, halogen or trifluoromethyl, R3 is hydrogen, 1–4C-alkyl, R4-substituted 1–4C-alkyl, 1–4C-alkylcarbonyl, 2–4C-alkenyl-carbonyl, halo-1–4C-alkylcarbonyl, N(R14)R15-1–4C-alkyl-carbonyl, di-1–4C-alkylcarbamoyl or 1–4C-alkyl-sulfonyl, R4 is hydroxyl, 1–4C-alkoxy, carboxyl, 1–4C-alkoxy-carbonyl or —N(R14)R15, R5 is hydrogen, 1–4C-alkyl or 1–4C-alkoxy, R6 is 1–7C-alkyl, 3–7C-cycloalkyl, 3–7C-alkenyl, R8- and R9-substituted phenyl or the radical $C_mH_{2m}$—R6a, R6a is a mono- or di-1–4C-alkylcarbamoyl or -thiocarbamoyl radical, an N-1–4C-alkyl-N'-cyano-amidino radical, a 1-N-1–4C-alkylamino-2-nitroethylene radical, an N-2-propynyl-N'-cyano-amidino radical, an aminosulfonyl-amidino radical, or an R8- and R9-substituted cyclic or bicyclic radical which is chosen from the group consisting of a radical of one of benzene, furan, thiophene, pyrrole, oxazole, isoxazole, thiazole, thiazoline, isothiazole, imidazole, imidazoline, pyrazole, triazole, tetrazole, thiadiazole, thiadiazole 1-oxide, oxadiazole, pyridine, pyridine N-oxide, pyrimidine, triazine, pyridone, benzimidazole, imidazopyridine, benzothiazole and benzoxazole, R7 is hydrogen, 1–4C-alkyl or 1–4C-alkoxy, R8 is hydrogen, 1–4C-alkyl, hydroxyl, 1–4C-alkoxy, halogen, nitro, guanidino, carboxyl, 1–4C-alkoxycarbonyl, R10-substituted 1–4C-alkyl or —N(R11)R12, R9 is hydrogen, 1–4C-alkyl, hydroxyl, 1–4C-alkoxy, fluorine or trifluoromethyl, R10 is hydroxyl, 1–4C-alkoxy, carboxyl, 1–4C-alkoxycarbonyl or —N(R11)R12, in which R11 is hydrogen, 1–4C-alkyl or —CO—R13 and R12 is hydrogen or 1–4C-alkyl, or in which R11 and R12, together and including the nitrogen atom to which they are both bonded, are a piperidino or morpholino radical, R13 is hydrogen, 1–4C-alkyl or 1–4C-alkoxy, R14 is 1–4C-alkyl and R15 is 1–4C-alkyl, or in which R14 and R15, together and including the nitrogen atom to which they are both bonded, are a piperidino or morpholino radical, n is the number 0 or 1, m is a number from 1 to 7 and X is CH or N, and their salts, excluding those compounds of the formula I in which X is CH and at the same time R1 is hydrogen, 1–4C-alkyl or 1–4C-alkoxy, R3 is hydrogen or 1–4C-alkyl, R6a is an R8- and R9-substituted cyclic or bicyclic radical which is chosen from the group consisting of a radical of one of benzene, furan, thiophene, pyrrole, oxazole, isoxazole, thiazole, isothiazole, imidazole, pyrazole, triazole, tetrazole, thiadiazole, pyridine and pyrimidine, R8 is hydrogen, 1–4C-alkyl, 1–4C-alkoxy, halogen, guanidino, R10-substituted 1–4C-alkyl or —N(R11)R12, R9 is hydrogen, 1–4C-alkyl, 1–4C-alkoxy, fluorine or trifluoromethyl, R10 is hydroxyl, 1–4C-alkoxy or —N(R11)R12 and R2, R5, R6, R7, R11, R12, R13, R14, R15, n and m have one of the aforementioned meanings.

1–4C-alkyl is straight-chain or branched alkyl radicals having 1 to 4 carbon atoms. Examples which may be mentioned are the butyl, iso-butyl, sec-butyl, tert-butyl, propyl, isopropyl, ethyl and the methyl radical.

1–4C-alkoxy is a radical which, in addition to the oxygen atom, contains one of the abovementioned 1–4C-alkyl radicals. Examples which may be mentioned are the methoxy and the ethoxy radical.

Halogen in the context of the present invention is bromine, chlorine and, in particular, fluorine.

1–4C-alkylcarbonyl is a radical which, in addition to the carbonyl group, contains one of the abovementioned 1–4C-alkyl radicals. An example which may be mentioned is the acetyl radical.

2–4C-alkenylcarbonyl is a radical which, in addition to the carbonyl group, contains a 2–4C-alkenyl radical, for example a propenyl radical or a butenyl radical. An example which may be mentioned is the acryloyl radical.

Halo-1–4C-alkylcarbonyl is a radical which, in addition to the carbonyl group, contains a halogen-substituted 1–4C-alkyl radical. An example which may be mentioned is the γ-chlorobutyryl radical.

N(R15)R16-1–4C-alkylcarbonyl is a radical which, in addition to the carbonyl group, contains an —N(R15)R16-substituted 1–4C-alkyl radical. An example which may be mentioned is the 3-dimethylamino-propionyl radical.

Di-1–4C-alkylcarbamoyl is a radical which, in addition to the carbonyl group, contains a di-1–4C-alkylamino radical. The di-1–4C-alkylamino radical is an amino radical which is substituted by two identical or different radicals of the abovementioned 1–4C-alkyl radicals. Examples which may be mentioned are the dimethylamino, the diethylamino and the di-isopropylamino radical. The dimethylcarbamoyl and the diethylcarbamoyl radical may be mentioned as examples of di-1–4C-alkylcarbamoyl radicals.

1–4C-alkylsulfonyl is a radical which, in addition to the sulfonyl group ($-SO_2-$), contains one of the abovementioned 1–4C-alkyl radicals. An example which may be mentioned is the methylsulfonyl radical.

1–4C-alkoxycarbonyl is a radical which, in addition to the carbonyl group, contains one of the abovementioned 1–4C-alkoxy radicals. Examples which may be mentioned are the methoxycarbonyl and the ethoxycarbonyl radical.

Examples which may be mentioned of R4-substituted 1–4C-alkyl radicals are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the dimethylaminomethyl and the 2-dimethylaminoethyl radical.

1–7C-alkyl for R6 is straight-chain or branched alkyl radicals having 1 to 7 carbon atoms. Examples which may be mentioned are the heptyl, isoheptyl (2-methylhexyl), hexyl, isohexyl(2-methylpentyl), neohexyl(2,2-dimethylbutyl), pentyl, isopentyl-(3-methylbutyl), neopentyl(2,2-dimethylpropyl), butyl, isobutyl, sec-butyl, tert-butyl, propyl, isopropyl, ethyl and the methyl radical.

3–7C-cycloalkyl is cycloalkyl radicals having 3 to 7 carbon atoms, that is to say the cyclopropyl, the cyclobutyl, the cyclopentyl, the cyclohexyl and the cycloheptyl radical.

3–7C-alkenyl is a straight-chain or branched alkenyl radical having 3 to 7 carbon atoms. Preferred 3–7C-alkenyl radicals which may be mentioned are the 2-butenyl, the 3-butenyl, the 1-propenyl and the 2-propenyl radical (allyl radical).

Mono- or di-1–4C-alkylcarbamoyl radicals are carbamoyl radicals ($-CO-NH_2$) which are substituted by one or two identical or different radicals of the abovementioned 1–4C-alkyl radicals. Examples which may be mentioned are the methylcarbamoyl, the isopropylcarbamoyl and the dimethylcarbamoyl radical.

Mono- or di-1–4C-alkylthiocarbamoyl radicals are thiocarbamoyl radicals ($-CS-NH_2$) which are substituted by one or two identical or different radicals of the abovementioned 1–4C-alkyl radicals. Examples which may be mentioned are the methylthiocarbamoyl, the isopropylthiocarbamoyl and the dimethylthiocarbamoyl radical.

The N-methyl-N'-cyano-amidino radical [$-C(=NCN)-NH-CH_3$] may be mentioned, in particular, as an example of the N-1–4C-alkyl-N'-cyano-amidino radical.

The 1-N-methylamino-2-nitroethylene radical [$-C(NCH_3)=CHNO_2$] may be mentioned, in particular, as an example of a 1-N-1–4C-alkylamino-2-nitroethylene radical.

The following radicals may be mentioned as examples of cyclic or bicyclic radicals R6a: phenyl, 2-furyl, 3-furyl, 2-thienyl, 3-thienyl, 3-pyrrolyl, 2-oxazolyl, 4-oxazolyl, 4-isoxazolyl, 5-isoxazolyl, 2-thiazolyl, 3-isothiazolyl, 2-imidazolyl, 3-pyrazolyl, 4-pyrazolyl, 1,2,3-triazol-4-yl, 1,2,5-thiadiazol-4-yl, 1,2,5-thiadiazol-4-yl 1-oxide, 1,2,4-thiazol-3-yl, tetrazol-5-yl, 1,3,4-thiadiazol-2-yl, 1,2,3-thiadiazol-4-yl, 1,2,5-thiadiazol-4-yl, 1,2,5-thiadiazol-4-yl 1-oxide, 1,3,4-oxadiazol-2-yl, 2-pyridyl, 4-pyridyl, 2-pyrimidinyl, 1,3,4-triazin-2-yl, 2-benzimidazolyl, 2-imidazopyridyl, 2-benzothiazolyl and 2-benzoxazolyl.

The substituents R8 and R9 can be bonded to any conceivable position in the cyclic and bicyclic radicals R6a. Examples which may be mentioned of R8-and R9-substituted radicals R6a are: 4-methylphenyl, 3-dimethylaminomethylphenyl, 3-piperidinomethylphenyl, 3-carboxymethylphenyl, 2-dimethylaminomethyl-5-methyl-3-furyl, 1-methylpyrrol-3-yl, 4,5-dimethyl-oxazol-2-yl, 3,5-dimethyl-isoxazol-4-yl, 4,5-dimethyl-thiazol-2-yl, 4-methyl-5-carboxyrmethyl-thiazol-2-yl, 1-methyl-imidazol-2-yl, 1-methyl-pyrazol-3-yl, 1-(2-dimethylaminoethyl)-pyrazol-3-yl, 5-methyl-1,3,4-oxadiazol-2-yl, 1-methyl-1,2,3-triazol-4-yl, 1-methyl-1,2,4-triazol-3-yl, 1-(2-dimethylaminoethyl)-1,2,3-triazol-4-yl, 1-methyl-tetrazol-5-yl, 1-(2-dimethylaminoethyl)-tetrazol-5-yl, 1-carboxymethyl-tetrazol-5-yl, 5-methyl-1,3,4-thiadiazol-2-yl, 5-trifluoromethyl-1,3,4-thiadiazol-2-yl, 1-(2-hydroxyethyl)-tetrazol-5-yl, 2-amino-1,3,4-thiadiazol-2-yl, 3-amino-1,2,4-triazol-5-yl, 4-methyl-5-trifluoromethyl-1,2,4-triazol-3-yl, 4-amino-pyrimidin-2-yl, 3-methyl-2-furyl, 2-methyl-3-furyl, 5-methyl-2-furyl, 5-ethyl-2-furyl, 3-methoxy-2-furyl, 5-dimethylaminomethyl-2-furyl, 5-N-morpho-linomethyl-2-furyl, 5-methoxymethyl-2-furyl, 5-hydroxymethyl-2-furyl, 5-N-piperidinomethyl-2-furyl, 5-chloro-2-furyl, 5-fluoro-2-furyl, 5-methyl-2-thienyl, 5-chloro-2-thienyl 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrrolyl, 2,5-di-methyl-1-pyrrolyl, 1,5-dimethyl-2-pyrrolyl, 1-methyl-2-pyrrolyl, 2-amino-4-thiazolyl, 2-methyl-4-thiazolyl, 2-amino-5-methyl-4-thiazolyl, 4-methyl-5-thiazolyl, 2-dimethylaminomethyl-4-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 2-methyl-4-imidazolyl, 5-methyl-4-imidazolyl, 2-methyl-1-imidazolyl, 4,5-dimethyl-2-imidazolyl, 4-hydroxymethyl-5-methyl-1-imidazolyl, 3-methyl-1-pyrazolyl, 5-amino-1,2,4-thiadiazol-3-yl, 4-methoxy-2-pyridinyl, 4-methoxy-3-methyl-2-pyridinyl and 3,4-dimethoxypyridinyl.

Possible radicals $-C_mH_{2m}$ which are substituted by R6a are straight-chain or branched radicals. Examples which may be mentioned are the heptyl, isoheptyl(2-methylhexyl), hexyl, isohexyl(2-methylpentyl), neohexyl(2,2-dimethylbutyl), pentyl isopentyl(3-methylbutyl-yl), neopentyl(2,2-dimethylpropyl), butyl, isobutyl, sec-butyl, tert-butyl, propyl, isopropyl, ethyl and the methyl radical. The following radicals may be mentioned as examples of radicals $-C_mH_{2m}-R6a$: 3-methyl-2-furyl-methyl, 3-methyl-2-furyl-ethyl, 2-furyl-methyl, 2-furyl-ethyl, 2-furyl-propyl, 2-furyl-butyl, 5-dimethylaminomethyl-2-furyl-methyl, 5-dimethylaminomethyl-2-furyl-ethyl, 5-dimethylaminomethyl-2-furyl-propyl, 2-methyl-3-furyl-methyl, 2-methyl-3-furyl-ethyl, 5-N-morpholinomethyl-2-furyl-methyl, 5-N-morpholinomethyl-2-furyl-ethyl, 5-N-piperidinomethyl-2-furyl-methyl, 5-N-piperidinomethyl-2-furyl-ethyl, 3-methoxy-2-furyl-methyl, 3-methoxy 2-furyl-ethyl, 3-amino-2-thienyl-methyl, 3-amino-2-thienyl-ethyl, 3-guanidino-2-thienyl-methyl, 5-dimethylaminomethyl-2-thienyl-methyl, 5-N-morpholino-methyl-2-thienyl-methyl, 1-methyl-2-pyrrolyl-methyl, 2-amino-4-thiazolyl-methyl, 2-dimethylaminomethyl-4-thiazolyl-methyl, 2-guanidino-4-thiazolyl-methyl, 2-N-morpholinomethyl-4-thiazolyl-methyl, 5-methyl-4-imidazolyl-methyl, 4-hydroxymethyl-5-methyl-1-imidazolyl-methyl, 3-guanidino-2-thienyl-ethyl, 5-dimethylaminomethyl-2-thienyl-ethyl, 5-N- morpholinomethyl-2-thienyl-ethyl, 1-methyl-2-pyrrolyl-ethyl, 2-amino-4-thiazolyl-ethyl, 2-dimethylaminomethyl-4-thiazolyl-ethyl, 2-guanidino-4-thiazolyl-ethyl, 2-N-morpholino-methyl-4-thiazolyl-ethyl, 5-methyl-4-imidazolyl-ethyl, 4-hydroxymethyl-5-methyl-1-imidazolyl-ethyl, 5-amino-(1,2,4-thiadiazol-3-yl)-methyl, 5-amino-(1,2,4-thiadiazol-3-yl)-ethyl, (1,2,5-thiadiazol-4-yl)-ethyl, (1,2,5-thiadiazol-4-yl)-propyl, 2-pyridylethyl, 2-pyridyl-propyl, 4-pyridylpropyl, 4-pyridylmethyl, 5,6-dihydroxy-(1, 3,4-triazin-2-yl)-methyl, 2-benzimidazolylethyl, 2-imidazopyridyl-methyl, dimethylthiocarbamoylmethyl, dimethylthiocarbamoyl-ethyl, isopropylthiocarbamoyl-ethyl, N-methyl-N'cyano-amidino-methyl [—CH$_2$—C(=NCN)NH—CH$_3$], N-methyl-N'-cyano-amidino-ethyl [—CH$_2$CH$_2$—C(=NCN)NH—CH$_3$], 3-N-methylamino-4-nitro-but-3-en-1-yl [—CH$_2$CH$_2$—C(NHCH$_3$)=CHNO$_2$], N-2-propynyl-N'-cyanoamidino-ethyl [—CH$_2$CH$_2$—C(=NCH) NH—CH$_2$C≡CH] and aminosulfonylamidno-ethyl [—CH$_2$CH$_2$—C(NH$_2$)=N—SO$_2$—NH$_2$].

Possible salts of compounds of the formula I in which n is the number 0 are all acid addition salts. The pharmacologically tolerated salts of the inorganic and organic acids usually used in pharmaceutical formulation may be mentioned in particular. Salts which are not tolerated pharmacologically and which may be initially obtained as process products, for example, during preparation of the compounds according to the invention on an industrial scale are converted into pharmacologically tolerated salts by processes known to the expert. Suitable such salts are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, maleic acid, fumaric arid, succinic acid, oxalic acid, tartaric acid, embonic acid, stearic acid, toluenesulfonic acid, methanesulfonic acid or 3-hydroxy-2-naphthoic acid, the acids being employed in the preparation of the salt in a ratio of amounts which is equimolar or deviates therefrom—depending on whether the acid is mono- or polybasic and depending on which salt is desired.

For compounds of the formula I in which n is the number 1 and/or for compounds with a carboxyl radical, possible salts are also salts with bases. Examples which may be mentioned of basic salts are lithium, sodium, potassium, calcium, aluminum, magnesium, titanium, ammonium, meglumin or guanidinium salts, here also the bases being employed in the salt preparation in a ratio of amounts which is equimolar or deviates therefrom.

One embodiment of the invention relates to compounds of the formula I in which X is CH.

Another embodiment of the invention relates to compounds of the formula I in which X is N.

Another embodiment of the invention relates to compounds of the formula I in which R3 is R4-substituted 1–4C-alkyl, 1–4C-alkylcarbonyl, 2–4C-alkenylcarbonyl, halo-1–4C-alkylcarbonyl, N(R14)R15-1–4C-alkylcarbonyl, di-1–4C-alkylcarbamoyl or 1–4C-alkylsulfonyl.

Another embodiment of the invention relates to compounds of the formula I in which R6a is a mono- or di-1–4C-alkylcarbamoyl or -thiocarbamoyl radical, an N-1–4C-alkyl-N'-cyano-amidino radical, a 1-N-1–4C-alkylamino-2-nitro-ethylene radical, an N-2-propynyl-N'-cyano-amido radical or an aminosulfonylamidno radical.

Another embodiment of the invention relates to compounds of the formula I in which X is CH and R3 is R4-substituted 1–4C-alkyl, 1–4C-alkylcarbonyl, 2–4C-alkenylcarbonyl, halogen-1–4C-alkylcarbonyl, N(R14)R15-1–4C-alkylcarbonyl, di-1–4C-alkylcarbamoyl or 1–4C-alkylsulfonyl.

Another embodiment of the invention relates to compounds of the formula I in which X is CH and R6a is a mono- or di-1–4C-alkylcarbamoyl or -thiocarbamoyl radical, an N-1–4C-alkyl-N'-cyano-amidino radical, a 1-N-1–4C-alkylamino-2-nitroethylene radical, an N-2-propynyl-N'-cyano-amidino radical or an aminosulfonyl-amidino radical.

Compounds of the formula I which are to be singled out are those in which

R1 is hydrogen, 1–4C-alkoxy or halogen,

R2 is hydrogen, 1–4C-alkyl, 1–4C-alkoxy or halogen,

R3 is hydrogen, 1–4C-alkyl, R4-substituted 1–4C-alkyl, 1–4C-alkylcarbonyl, 2–4C-alkenylcarbonyl, halogeno-1–4C-alkylcarbonyl, N(R14)R15-1–4C-alkylcarbonyl, di-1–4C-alkylcarbamoyl or 1–4C-alkylsulfonyl, R4 is hydroxyl, carboxyl, 1–4C-alkoxycarbonyl or —N(R14)R15, R5 is hydrogen, 1–4C-alkyl or 1–4C-alkoxy, R6 is R8- and R9-substituted phenyl or the radical $C_mH_{2m}$—R6a, R6a is a mono- or di-1–4C-alkylcarbamoyl or -thiocarbamoyl radical, an N-1–4C-alkyl-N'-cyano-amidino radical, a 1-N-1–4C-alkylamino-2-nitroethylene radical, an N-2-propynyl-N'-cyano-amidino radical, an aminosulfonyl-amidino radical, or an R8- and R9-substituted cyclic or bicyclic radical which is chosen from the group consisting of a radical of one of benzene, furan, thiophene, thiazole, isothiazole, imidazole, pyrazole, triazole, tetrazole, thiadiazole, oxadiazole, pyridine, pyrimidine, triazine, pyridone, benzimidazole and imidazopyridine, R7 is hydrogen or 1–4C-alkyl, R8 is hydrogen, 1–4C-alkyl, hydroxyl, nitro, guanidino, carboxyl, 1–4C-alkoxycarbonyl or R10-substituted 1–4C-alkyl, R9 is hydrogen, 1–4C-alkyl, hydroxyl, 1–4C-alkoxy or fluorine, R10 is hydroxyl, 1–4C-alkoxy, carboxyl, 1–4C-alkoxycarbonyl or —N(R11)R12, in which R11 is 1–4C-alkyl or —CO—R13 and R12 is 1–4C-alkyl, or in which R11 and R12, together and including the nitrogen atom to which they are both bonded, are a piperidino or morpholino radical, R13 is 1–4C-alkyl, R14 is 1–4C-alkyl and R15 is 1–4C-alkyl, or in which R14 and R15, together and including the nitrogen atom to which they are both bonded, are a piperidino or morpholino radical, n is the number 0 or 1, m is a number from 1 to 4 and X is CH or N, and their salts, excluding those compounds of the formula I in which X is CH and at the same time R1 is hydrogen or 1–4C-alkoxy, R3 is hydrogen or 1–4C-alkyl, R6a is an R8- and R9-substituted cyclic radical which is chosen from the group consisting of a radical of one of benzene, furan, thiophene, thiazole, isothiazole, imidazole, pyrazole, triazole, tetrazole, thiadiazole, pyridine and pyrimidine, R8 is hydrogen, 1–4C-alkyl, guanidino or R10-substituted 1–4C-alkyl, R9 is hydrogen, 1–4C-alkyl, 1–4C-alkoxy or fluorine, R10 is hydroxyl, 1–4C-alkoxy or —N(R11)R12 and R2, R5, R6, R7, R11, R12, R13, R14, R15, n and m have one of the abovementioned meanings.

Compounds of the formula I which are to be emphasized in particular are those in which R1 is hydrogen, 1–4C-alkoxy or halogen, R2 is hydrogen or halogen, R3 is hydrogen, R4-substituted 1–4C-alkyl, 1–4C-alkylcarbonyl, 2–4C-alkenylcarbonyl, halo-1–4C-alkylcarbonyl, N(R14)R15-1–4C-alkylcarbonyl, di-1–4C-alkylcarbamoyl or 1–4C-alkylsulfonyl, R4 is carboxyl, 1–4C-alkoxycarbonyl or —N(R14)R15, R5 is 1–4C-alkyl or 1–4C-alkoxy, R6 is R8- and R9-substituted phenyl or the radical $C_mH_{2m}$—R6a, R6a is a mono- or di-1–4C-alkylcarbamoyl or -thiocarbamoyl radical, an N-1–4C-alkyl-N'-cyano-amidino radical, a 1-N-1–4C-alkylamino-2-nitroethylene radical or an R8- and R9-substituted cyclic or bicyclic radical which is chosen from the group consisting of a radical of one of benzene, furan, thiophene, thiazole, isothiazole, imidazole, pyrazole, triazole, tetrazole, thiadiazole, oxadiazole, pyridine, pyrimidine, triazine, pyridone, benzimidazole and imidazopyridine, R7 is hydrogen or 1–4C-alkyl, R8 is hydrogen, 1–4C-alkyl, hydroxyl, nitro, guanidino, carboxyl, 1–4C-alkoxycarbonyl or R10-substituted 1–4C-alkyl, R9 is hydrogen, 1–4C-alkyl, hydroxyl or fluorine, R10 is hydroxyl, 1–4C-alkoxycarbonyl or —N(R11)R12, in which R11 is 1–4C-alkyl and R12 is 1–4C-alkyl, or in which R11 and R12, together and including the nitrogen atom to which they are both bonded, are a piperidino or morpholino radical, R14 is 1–4C-alkyl and R15 is 1–4C-alkyl, or in which R14 and R15, together and including the nitrogen atom to which they are both bonded, are a piperidino or morpholino radical, n is the number 0 or 1, m is a number from 1 to 4 and X is CH or N, and their salts, excluding those compounds of the formula I in which X is CH and at the same time R1 is hydrogen or 1–4C-alkoxy, R3 is hydrogen, R6a is an R8- and R9-substituted cyclic radical which is chosen from the group consisting of a radical of one of benzene, furan, thiophene, thiazole, isothiazole, imidazole, pyrazole, triazole, tetrazole, thiadiazole, pyridine and pyrimidine, R8 is hydrogen, 1–4C-alkyl, guanidino or R10-substituted 1–4C-alkyl, R9 is hydrogen, 1–4C-alkyl or fluorine, R10 is hydroxyl or —N(R11)R12 and R2, R5, R6, R7, R11, R12, R13, R14, R15, n and m have one of the abovementioned meanings.

Preferred compounds of the formula I are those in which

R1 is hydrogen, 1–4C-alkoxy or fluorine,

R2 is hydrogen or fluorine,

R3 is hydrogen, R4-substituted 1–4C-alkyl, N(R14)R15-1–4C-alkylcarbonyl, di-1–4C-alkylcarbamoyl or 1–4C-alkylsulfonyl, R4 is 1–4C-alkoxycarbonyl or —N(R14)R15, R5 is 1–4C-alkyl, R6 is R8- and R9-substituted phenyl or the radical $C_mH_{2m}$—R6a, R6a is an R8- and R9-substituted cyclic radical which is chosen from the group consisting of a radical of one of benzene, furan, thiophene, thiazole, imidazole, triazole, tetrazole, pyridine and triazine, R7 is hydrogen, R8 is hydrogen, nitro, 1–4C-alkoxycarbonyl or R10-substituted 1–2C-alkyl, R9 is hydrogen or 1–4C-alkyl, R10 is 1–4C-alkoxycarbonyl or —N(R11)R12, in which R11 is 1–4C-alkyl and R12 is 1–4C-alkyl, or in which R11 and R12, together and including the nitrogen atom to which they are both bonded, are a piperidino or morpholino radical, R14 is 1–4C-alkyl and R15 is 1–4C-alkyl, or in which R14 and R15, together and including the nitrogen atom to which they are both bonded, are a piperidino or morpholino radical, n is the number 0, m is a number from 1 to 4 and X is CH or N, and their salts, excluding those compounds of the formula I in which X is CH and at the same time R1 is hydrogen or 1–4C-alkoxy, R3 is hydrogen, R6a is an R8- and R9-substituted cyclic radical which is chosen from the group consisting of a radical of one of benzene, furan, thiophene, thiazole, imidazole, triazole, tetrazole and pyridine, R8 is hydrogen, or R10-substituted 1–2C-alkyl, R9 is hydrogen or 1–4C-alkyl, R10 is —N(R11)R12 and R2, R5, R6, R7, R11, R12, R13, R14, R15, n and m have one of the abovementioned meanings.

One embodiment of the preferred compounds is those in which X is CH.

Another embodiment of the preferred compounds is those in which X is N.

Another embodiment of the preferred compounds is those in which R3 is R4-substituted 1–4C-alkyl, N(R14)R15-1–4C-alkylcarbonyl, di-1–4C-alkylcarbamoyl or 1–4C-alkylsulfonyl.

Another embodiment of the preferred compounds is those in which X is CH and R3 is R4-substituted 1–4C-alkyl, N(R14)R15-1–4C-alkylcarbonyl, di-1–4C-alkylcarbamoyl or 1–4C-alkylsulfonyl.

Particularly preferred compounds of the formula I are those in which

R1 is hydrogen,

R2 is hydrogen,

R3 is hydrogen,

R5 is 1–4C-alkyl,

R6 is the radical $C_mH_{2m}$—R6a,

R6a is an R8- and R9-substituted cyclic radical which is chosen from the group consisting of a radical of one of benzene, furan, thiophene, thiazole, imidazole, triazole, tetrazole, pyridine and triazine, R7 is hydrogen, R8 is nitro, R9 is hydrogen or 1–4C-alkyl, n is the number 0, m is a number from 1 to 4 and X is CH or N, and their salts.

Very particularly preferred compounds of the formula I are those in which

R1 is hydrogen,

R2 is hydrogen,

R3 is hydrogen,

R5 is 1–4C-alkyl,

R6 is the radical $C_mH_{2m}$—R6a,

R6a is an R8- and R9-substituted cyclic radical which is chosen from the group consisting of a radical of one of furan, imidazole and thiazole, R7 is hydrogen, R8 is nitro, R9 is hydrogen or 1–4C-alkyl, n is the number 0, m is a number from 1 to 4 and X is CH or N, and their salts.

Examples of compounds according to the invention are listed in the following tables:

TABLE 1

Compounds of the formula I (see attached formula sheet I) where X = N, R6 = $C_mH_{2m}$-R6a, n = 0 and the following further substituent definitions:

| R1 | R2 | R3 | R5 | R6a | R7 | m |
|---|---|---|---|---|---|---|
| H | H | H | H | 2-Furyl | H | 1 |
| H | H | H | H | 2-Thienyl | H | 1 |
| H | H | H | H | 3-Thienyl | H | 1 |
| H | H | H | H | 5-Dimethylaminomethyl-2-furyl | H | 1 |
| H | H | H | H | 5-Piperidinomethyl-2-furyl | H | 1 |
| H | H | H | H | 5-Dimethylaminomethyl-2-thienyl | H | 1 |
| H | H | H | H | 2-Amino-4-thiazolyl | H | 1 |
| H | H | H | H | 2-Dimethylaminomethyl-4-thiazolyl | H | 1 |
| H | H | H | H | 2-Guanidino-4-thiazolyl | H | 1 |
| H | H | H | H | 2-Formylamino-4-thiazolyl | H | 1 |
| H | H | H | H | 4-Methyl-5-oxazolyl | H | 1 |
| H | H | H | H | 2-Methyl-4-imidazolyl | H | 1 |
| H | H | H | H | 5-Methyl-4-imidazolyl | H | 1 |
| H | H | H | H | 5-Amino-1,2,4-thiadiazol-3-yl | H | 1 |
| H | OCH$_3$ | H | H | 2-Furyl | H | 1 |
| H | OCH$_3$ | H | H | 2-Thienyl | H | 1 |
| H | OCH$_3$ | H | H | 5-Dimethylaminomethyl-2-furyl | H | 1 |
| H | OCH$_3$ | H | H | 5-Dimethylaminomethyl-2-thienyl | H | 1 |
| H | OCH$_3$ | H | H | 2-Amino-4-thiazolyl | H | 1 |

TABLE 1-continued

Compounds of the formula I (see attached formula sheet I) where X = N, R6 = $C_mH_{2m}$-R6a, n = 0 and the following further substituent definitions:

| R1 | R2 | R3 | R5 | R6a | R7 | m |
|---|---|---|---|---|---|---|
| H | OCH$_3$ | H | H | 2-Dimethylamino-4-thiazolyl | H | 1 |
| H | OCH$_3$ | H | H | 2-Guanidino-4-thiazolyl | H | 1 |
| H | OCH$_3$ | H | H | 2-Formylamino-4-thiazolyl | H | 1 |
| H | OCH$_3$ | H | H | 4-Methyl-5-thiazolyl | H | 1 |
| H | OCH$_3$ | H | H | 4-Methyl-5-oxazolyl | H | 1 |
| H | OCH$_3$ | H | H | 2-Methyl-4-imidazolyl | H | 1 |
| H | OCH$_3$ | H | H | 5-Methyl-4-imidazolyl | H | 1 |
| H | H | H | CH$_3$ | 2-Furyl | H | 1 |
| H | H | H | CH$_3$ | 2-Thienyl | H | 1 |
| H | H | H | CH$_3$ | 5-Dimethylaminomethyl-2-furyl | H | 1 |
| H | H | H | CH$_3$ | 5-Dimethylaminomethyl-2-thienyl | H | 1 |
| H | H | H | CH$_3$ | 2-Amino-4-thiazolyl | H | 1 |
| H | H | H | CH$_3$ | 2-Dimethylaminomethyl-4-thiazolyl | H | 1 |
| H | H | H | CH$_3$ | 2-Guanidino-4-thiazolyl | H | 1 |
| H | H | H | CH$_3$ | 2-Formylamino-4-thiazoyl | H | 1 |
| H | H | H | CH$_3$ | 4-Methyl-5-oxazolyl | H | 1 |
| H | H | H | CH$_3$ | 2-Methyl-4-imidazolyl | H | 1 |
| H | H | H | CH$_3$ | 5-Methyl-4-imidazolyl | H | 1 |
| H | F | H | CH$_3$ | 2-Furyl | H | 1 |
| F | H | H | H | 2-Furyl | H | 1 |
| F | H | H | H | 2-Thienyl | H | 1 |
| F | H | H | H | 5-Dimethylaminomethyl-2-furyl | H | 1 |
| F | H | H | H | 5-Dimethylaminomethyl-2-thienyl | H | 1 |
| F | H | H | H | 2-Amino-4-thiazolyl | H | 1 |
| F | H | H | H | 2-Dimethylaminomethyl-4-thiazolyl | H | 1 |
| F | H | H | H | 2-Guanidino-4-thiazolyl | H | 1 |
| F | H | H | H | 2-Formylamino-4-thiazolyl | H | 1 |
| F | H | H | H | 4-Methyl-5-oxazolyl | H | 1 |
| F | H | H | H | 2-Methyl-4-imidazolyl | H | 1 |
| F | H | H | H | 5-Methyl-5-imidazolyl | H | 1 |
| H | F | H | OCH$_3$ | 2-Furyl | H | 1 |
| H | H | H | H | 2-Furyl | H | 2 |
| H | H | H | H | 2-Thienyl | H | 2 |
| H | H | H | H | 5-Dimethylaminomethyl-2-furyl | H | 2 |
| H | H | H | H | 5-Dimethylaminomethyl-thienyl | H | 2 |
| H | H | H | H | 2-Amino-4-thiazolyl | H | 2 |
| H | H | H | H | 2-Dimethylaminomethyl-4-thiazolyl | H | 2 |
| H | H | H | H | 2-Guanidino-4-thiazolyl | H | 2 |
| H | H | H | H | 2-Formylamino-4-thiazolyl | H | 2 |
| H | H | H | H | 4-Methyl-5-oxazolyl | H | 2 |
| H | H | H | H | 2-Methyl-4-imidazolyl | H | 2 |
| H | H | H | H | 5-Methyl-4-imidazolyl | H | 2 |
| H | OCH$_3$ | H | H | 2-Furyl | H | 2 |
| H | OCH$_3$ | H | H | 2-Thienyl | H | 2 |
| H | OCH$_3$ | H | H | 5-Dimethylaminomethyl-2-furyl | H | 2 |
| H | OCH$_3$ | H | H | 5-Dimethylaminoethyl-2-thienyl | H | 2 |
| H | OCH$_3$ | H | H | 2-Amino-4-thiazolyl | H | 2 |
| H | OCH$_3$ | H | H | 2-Dimethylaminomethyl-2-thiazolyl | H | 2 |
| H | OCH$_3$ | H | H | 2-Guanidino-4-thiazolyl | H | 2 |
| H | OCH$_3$ | H | H | 2-Formylamino-4-thiazolyl | H | 2 |
| H | OCH$_3$ | H | H | 4-Methyl-5-oxazolyl | H | 2 |
| H | OCH$_3$ | H | H | 2-Methyl-4-imidazolyl | H | 2 |
| H | OCH$_3$ | H | H | 5-Methyl-4-imidazolyl | H | 2 |
| H | H | H | CH$_3$ | 2-Furyl | H | 2 |
| H | H | H | CH$_3$ | 2-Thienyl | H | 2 |
| H | H | H | CH$_3$ | 5-Dimethylaminomethyl-2-furyl | H | 2 |
| H | H | H | CH$_3$ | 5-Dimethylaminomethyl-2-thienyl | H | 2 |
| H | H | H | CH$_3$ | 5-Amino-4-thiazolyl | H | 2 |
| H | H | H | CH$_3$ | 2-Dimethylaminomethyl-4-thiazolyl | H | 2 |
| F | H | H | CH$_3$ | 2-Guanidino-4-thiazolyl | H | 2 |
| H | H | H | CH$_3$ | 2-Formylamino-4-thiazolyl | H | 2 |
| F | H | H | CH$_3$ | 4-Methyl-5-oxazolyl | H | 2 |
| F | H | H | CH$_3$ | 2-Methyl-4-imidazolyl | H | 2 |
| F | H | H | CH$_3$ | 5-Methyl-4-imidazolyl | H | 2 |
| F | H | H | H | 2-Furyl | H | 2 |
| F | H | H | H | 2-Thienyl | H | 2 |
| F | H | H | H | 5-Dimethylaminomethyl-2-furyl | H | 2 |
| F | H | H | H | 5-Dimethylaminomethyl-2-thienyl | H | 2 |

TABLE 1-continued

Compounds of the formula I (see attached formula sheet I) where X = N, R6 = $C_mH_{2m}$-R6a, n = 0 and the following further substituent definitions:

| R1 | R2 | R3 | R5 | R6a | R7 | m |
|---|---|---|---|---|---|---|
| F | H | H | H | 5-Amino-4-thiazolyl | H | 2 |
| F | H | H | H | 2-Dimethylaminomethyl-4-thiazolyl | H | 2 |
| F | H | H | H | 2-Guanidino-4-thiazolyl | H | 2 |
| F | H | H | H | 2-Formylamino-4-thiazolyl | H | 2 |
| F | H | H | H | 4-Methyl-4-oxazolyl | H | 2 |
| F | H | H | H | 2-Methyl-4-imidazolyl | H | 2 |
| F | H | H | H | 5-Methyl-4-imidazolyl | H | 2 |
| H | H | H | H | 3-Thienyl | H | 1 |
| H | OCH$_3$ | H | H | 3-Thienyl | H | 1 |
| H | H | H | CH$_3$ | 3-Thienyl | H | 1 |
| F | H | H | H | 3-Thienyl | H | 1 |
| H | H | H | H | 3-Thienyl | H | 2 |
| H | OCH$_3$ | H | H | 3-Thienyl | H | 2 |
| H | H | H | CH$_3$ | 3-Thienyl | H | 2 |
| F | H | H | H | 3-Thienyl | H | 2 |
| H | OCH$_3$ | H | H | 5-Piperidinomethyl-2-furyl | H | 1 |
| H | H | H | CH$_3$ | 5-Piperidinomethyl-2-furyl | H | 1 |
| F | H | H | H | 5-Piperidinomethyl-2-furyl | H | 1 |
| H | H | H | H | 5-Piperidinomethyl-2-furyl | H | 2 |
| H | OCH$_3$ | H | H | 5-Piperdinomethyl-2-furyl | H | 2 |
| H | H | H | CH$_3$ | 5-Piperdinomethyl-2-furyl | H | 2 |
| F | H | H | H | 5-Piperdinomethyl-2-furyl | H | 2 |
| H | OCH$_3$ | H | H | 5-Amino-1,2,4-thiadiazol-3-yl | H | 1 |
| H | H | H | CH$_3$ | 5-Amino-1,2,4-thiadiazol-3-yl | H | 1 |
| F | H | H | H | 5-Amino-1,2,4-thiadiazol-3-yl | H | 1 |
| H | H | H | H | 5-Amino-1,2,4-thiadiazol-3-yl | H | 2 |
| H | OCH$_3$ | H | H | 5-Amino-1,2,4-thiadiazol-3-yl | H | 2 |
| H | H | H | CH$_3$ | 5-Amino-1,2,4-thiadiazol-3-yl | H | 2 |
| F | H | H | H | 5-Amino-1,2,4-thiadiazol-3-yl | H | 2 |
| H | H | H | H | 4-Methyl-5-thiazolyl | H | 1 |
| H | H | H | CH$_3$ | 4-Methyl-5-thiazolyl | H | 1 |
| F | H | H | H | 4-Methyl-5-thiazolyl | H | 1 |
| H | H | H | H | 4-Methyl-5-thiazolyl | H | 2 |
| H | OCH$_3$ | H | H | 4-Methyl-5-thiazolyl | H | 2 |
| H | H | H | CH$_3$ | 4-Methyl-5-thiazolyl | H | 2 |
| F | H | H | H | 4-Methyl-5-thiazolyl | H | 2 |
| H | H | H | H | 5-Chloro-2-thienyl | H | 1 |
| H | OCH$_3$ | H | H | 5-Chloro-2-thienyl | H | 1 |
| F | H | H | H | 5-Chloro-2-thienyl | H | 1 |
| H | H | H | CH$_3$ | 5-Chloro-2-thienyl | H | 1 |
| H | H | H | H | 5-Chloro-2-thienyl | H | 2 |
| H | OCH$_3$ | H | H | 5-Chloro-2-thienyl | H | 2 |
| H | H | H | CH$_3$ | 5-Chloro-2-thienyl | H | 2 |
| H | H | H | H | 5-Chloro-2-thienyl | H | 3 |
| H | OCH$_3$ | H | H | 5-Chloro-2-thienyl | H | 3 |
| F | H | H | H | 5-Chloro-2-thienyl | H | 3 |
| H | H | H | CH$_3$ | 5-Chloro-2-thienyl | H | 3 |
| H | H | H | H | 2-Methyl-5-nitro-1-imidazolyl | H | 2 |
| H | OCH$_3$ | H | H | 2-Methyl-5-nitro-1-imidazolyl | H | 2 |
| F | H | H | CH$_3$ | 2-Methyl-5-nitro-1-imidazolyl | H | 2 |
| H | H | H | CH$_3$ | 2-Methyl-5-nitro-1-imidazolyl | H | 2 |
| H | H | H | H | 2-Methyl-5-nitro-1-imidazolyl | H | 3 |
| H | OCH$_3$ | H | H | 2-Methyl-5-nitro-1-imidazolyl | H | 3 |
| F | H | H | CH$_3$ | 2-Methyl-5-nitro-1-imidazolyl | H | 3 |
| H | H | H | CH$_3$ | 2-Methyl-5-nitro-1-imidazolyl | H | 3 |
| H | H | H | H | 5-Nitro-1-imidazolyl | H | 2 |
| H | OCH$_3$ | H | H | 5-Nitro-1-imidazolyl | H | 2 |
| F | H | H | CH$_3$ | 5-Nitro-1-imidazolyl | H | 2 |
| H | H | H | CH$_3$ | 5-Nitro-1-imidazolyl | H | 2 |
| H | H | H | H | 5-Nitro-1-imidazolyl | H | 3 |
| H | OCH$_3$ | H | H | 5-Nitro-1-imidazolyl | H | 3 |
| F | H | H | CH$_3$ | 5-Nitro-1-imidazolyl | H | 3 |
| H | H | H | CH$_3$ | 5-Nitro-1-imidazolyl | H | 3 |

TABLE 2

Compounds of the formula I (see attahed formula sheet I) where X = CH, R3 = COCH$_2$N(CH$_3$)$_2$, R6 = $C_mH_{2m}$-R6a, n = 0 and the following further substituent definitions:

| R1 | R2 | R5 | R6a | R7 | m |
|---|---|---|---|---|---|
| H | H | H | 2-Furyl | H | 1 |
| H | H | H | 2-Thienyl | H | 1 |
| H | H | H | 3-Thienyl | H | 1 |
| H | H | H | 5-Dimethylaminomethyl-2-furyl | H | 1 |
| H | H | H | 5-Piperidinomethyl-2-furyl | H | 1 |
| H | H | H | 5-Dimethylaminomethyl-2-thienyl | H | 1 |
| H | H | H | 2-Amino-4-thiazolyl | H | 1 |
| H | H | H | 2-Dimethylamonomethyl-4-thiazolyl | H | 1 |
| H | H | H | 2-Guanidino-4-thiazolyl | H | 1 |
| H | H | H | 2-Formylamino-4-thiazolyl | H | 1 |
| H | H | H | 4-Methyl-5-thiazolyl | H | 1 |
| H | H | H | 2-Methyl-4-imidazolyl | H | 1 |
| H | H | H | 5-Methyl-4-imidazolyl | H | 1 |
| H | H | H | 5-Amino-1,2,4-thiadiazol-3-yl | H | 1 |
| H | H | CH$_3$ | 2-Furyl | H | 1 |
| H | H | CH$_3$ | 2-Thienyl | H | 1 |
| H | H | CH$_3$ | 3-Thienyl | H | 1 |
| H | H | CH$_3$ | 5-Dimethylaminomethyl-2-furyl | H | 1 |
| H | H | CH$_3$ | 5-Piperidinomethyl-2-furyl | H | 1 |
| H | H | CH$_3$ | 5-Dimethylamonomethyl-2-thienyl | H | 1 |
| H | H | CH$_3$ | 2-Amino-4-thiazolyl | H | 1 |
| H | H | CH$_3$ | 5-Dimethylaminomethyl-4-thiazolyl | H | 1 |
| H | H | CH$_3$ | 2-Guanidino-4-thiazolyl | H | 1 |
| H | H | CH$_3$ | 2-Formylamino-4-thiazolyl | H | 1 |
| H | H | CH$_3$ | 4-Methyl-5-thiazolyl | H | 1 |
| H | H | CH$_3$ | 2-Methyl-4-imidazolyl | H | 1 |
| H | H | CH$_3$ | 5-Methyl-4-imidazolyl | H | 1 |
| H | H | CH$_3$ | 5-Amino-1,2,4-thiadiazol-3-yl | H | 1 |
| H | H | H | 2-Furyl | H | 2 |
| H | H | H | 2-Thienyl | H | 2 |
| H | H | H | 3-Thienyl | H | 2 |
| H | H | H | 5-Dimethylaminomethyl-2-furyl | H | 2 |
| H | H | H | 5-Piperidinomethyl-2-furyl | H | 2 |
| H | H | H | 5-Dimethylaminomethyl-2-thienyl | H | 2 |
| H | H | H | 2-Amino-4-thiazolyl | H | 2 |
| H | H | H | 2-Dimethylaminomethyl-4-thiazolyl | H | 2 |
| H | H | H | 2-Guanidino-4-thiazolyl | H | 2 |
| H | H | H | 2-Formylamino-4-thiazolyl | H | 2 |
| H | H | H | 4-Methyl-5-thiazolyl | H | 2 |
| H | H | H | 2-Methyl-4-imidazolyl | H | 2 |
| H | H | H | 5-Methyl-4-imidazolyl | H | 2 |
| H | H | H | 5-Amino-1,2,4-thiadiazol-3-yl | H | 2 |
| H | H | CH$_3$ | 2-Furyl | H | 2 |
| H | H | CH$_3$ | 2-Thienyl | H | 2 |
| H | H | CH$_3$ | 3-Thienyl | H | 2 |
| H | H | CH$_3$ | 5-Dimethylaminomethyl-2-furyl | H | 2 |
| H | H | CH$_3$ | 5-Piperidinomethyl-2-furyl | H | 2 |
| H | H | CH$_3$ | 5-Dimethylaminomethyl-2-thienyl | H | 2 |
| H | H | CH$_3$ | 2-Amino-4-thiazolyl | H | 2 |
| H | H | CH$_3$ | 2-Dimethylaminomethyl-4-thiazolyl | H | 2 |
| H | H | CH$_3$ | 2-Guanidino-4-thiazolyl | H | 2 |
| H | H | CH$_3$ | 2-Formylamino-4-thiazolyl | H | 2 |
| H | H | CH$_3$ | 4-Methyl-5-thiazolyl | H | 2 |
| H | H | CH$_3$ | 2-Methyl-4-imidazolyl | H | 2 |
| H | H | CH$_3$ | 5-Methyl-4-imidazolyl | H | 2 |
| H | H | CH$_3$ | 5-Amino-1,2,4-thiadiazol-3-yl | H | 2 |
| H | H | H | 5-Chloro-2-thienyl | H | 1 |
| H | H | CH$_3$ | 5-Chloro-2-thienyl | H | 1 |
| H | H | H | 5-Chloro-2-thienyl | H | 2 |
| H | H | CH$_3$ | 5-Chloro-2-theinyl | H | 2 |
| H | H | H | 2-Methyl-5-nitro-1-imidazolyl | H | 2 |
| H | H | CH$_3$ | 2-Methyl-5-nitro-1-imidazolyl | H | 2 |
| H | H | H | 2-Methyl-5-nitro-1-imidazolyl | H | 3 |
| H | H | CH$_3$ | 2-Methyl-5-nitro-1-imidazolyl | H | 3 |
| H | H | H | 5-Nitro-1-imidazolyl | H | 2 |
| H | H | CH$_3$ | 5-Nitro-1-imidazolyl | H | 2 |
| H | H | H | 5-Nitro-1-imidazolyl | H | 3 |
| H | H | CH$_3$ | 5-Nitro-1-imidazolyl | H | 3 |

TABLE 3

Compounds of the formula I (see attached formula sheet I) where X = CH, R3 = CH$_2$CH$_2$N(CH$_3$)$_2$, R6 = C$_m$H$_{2m}$-R6a, n = 0 and the following further substituent definitions:

| R1 | R2 | R5 | R6a | R7 | m |
|---|---|---|---|---|---|
| H | H | H | 2-Furyl | H | 1 |
| H | H | H | 2-Thienyl | H | 1 |
| H | H | H | 3-Thienyl | H | 1 |
| H | H | H | 5-Dimethylaminomethyl-2-furyl | H | 1 |
| H | H | H | 5-Piperidinomethyl-2-furyl | H | 1 |
| H | H | H | 5-Dimethylaminomethyl-2-thienyl | H | 1 |
| H | H | H | 2-Amino-4-thiazolyl | H | 1 |
| H | H | H | 2-Dimethylaminomethyl-4-thiazolyl | H | 1 |
| H | H | H | 2-Guanidino-4-thiazolyl | H | 1 |
| H | H | H | 2-Formylamino-4-thiazolyl | H | 1 |
| H | H | H | 4-Methyl-5-thiazolyl | H | 1 |
| H | H | H | 2-Methyl-4-imidazolyl | H | 1 |
| H | H | H | 5-Methyl-4-imidazolyl | H | 1 |
| H | H | H | 5-Amino-1,2,4-thiadiazol-3-yl | H | 1 |
| H | H | CH$_3$ | 2-Furyl | H | 1 |
| H | H | CH$_3$ | 2-Thienyl | H | 1 |
| H | H | CH$_3$ | 3-Thienyl | H | 1 |
| H | H | CH$_3$ | 5-Dimethylaminomethyl-2-furyl | H | 1 |
| H | H | CH$_3$ | 5-Piperidinomethyl-2-furyl | H | 1 |
| H | H | CH$_3$ | 5-Dimethylaminomethyl-2-thienyl | H | 1 |
| H | H | CH$_3$ | 2-Amino-4-thiazolyl | H | 1 |
| H | H | CH$_3$ | 2-Dimethylaminomethyl-4-thiazolyl | H | 1 |
| H | H | CH$_3$ | 2-Guanidino-4-thiazolyl | H | 1 |
| H | H | CH$_3$ | 2-Formylamino-4-thiazolyl | H | 1 |
| H | H | CH$_3$ | 4-Methyl-5-thiazolyl | H | 1 |
| H | H | CH$_3$ | 2-Methyl-4-imidazolyl | H | 1 |
| H | H | CH$_3$ | 5.-Methyl-4-imidazolyl | H | 1 |
| H | H | CH$_3$ | 5-Amino-1,2,4-thiadiazol-3-yl | H | 1 |
| H | H | H | 2-Furyl | H | 2 |
| H | H | H | 2-Thienyl | H | 2 |
| H | H | H | 3-Thienyl | H | 2 |
| H | H | H | 5-Dimethylaminomethyl-2-furyl | H | 2 |
| H | H | H | 5-Piperidinomethyl-2-furyl | H | 2 |
| H | H | H | 5-Dimethylaminomethyl-2-thienyl | H | 2 |
| H | H | H | 2-Amino-4-thiazolyl | H | 2 |
| H | H | H | 2-Dimethylaminomethyl-4-thiazolyl | H | 2 |
| H | H | H | 2-Guanidino-4-thiazolyl | H | 2 |
| H | H | H | 2-Formylamino-4-thiazolyl | H | 2 |
| H | H | H | 4-Methyl-5-thiazolyl | H | 2 |
| H | H | H | 2-Methyl-4-imidazolyl | H | 2 |
| H | H | H | 5-Methyl-4-imidazolyl | H | 2 |
| H | H | H | 5-Amino-1,2,4-thiadiazol-3-yl | H | 2 |
| H | H | CH$_3$ | 2-Furyl | H | 2 |
| H | H | CH$_3$ | 2-Thienyl | H | 2 |
| H | H | CH$_3$ | 3-Thienyl | H | 2 |
| H | H | CH$_3$ | 5-Dimethylaminomethyl-2-furyl | H | 2 |
| H | H | CH$_3$ | 5-Piperidinomethyl-2-furyl | H | 2 |
| H | H | CH$_3$ | 5-Dimethylaminomethyl-2-thienyl | H | 2 |
| H | H | CH$_3$ | 2-Amino-4-thaizolyl | H | 2 |
| H | H | CH$_3$ | 2-Dimethylaminomethyl-4-thiazolyl | H | 2 |
| H | H | CH$_3$ | 2-Guanidino-4-thiazolyl | H | 2 |
| H | H | CH$_3$ | 2-Formylamino-4-thiazolyl | H | 2 |
| H | H | CH$_3$ | 4-Methyl-5-thiazolyl | H | 2 |
| H | H | CH$_3$ | 2-Methyl-4-imidazolyl | H | 2 |
| H | H | CH$_3$ | 5-Methyl-4-imidazolyl | H | 2 |
| H | H | CH$_3$ | 5-Amino-1,2,4-thiadiazol-3-yl | H | 2 |
| H | H | H | 5-Chloro-2-thienyl | H | 1 |
| H | H | CH$_3$ | 5-Chloro-2-thienyl | H | 1 |
| H | H | H | 5-Chloro-2-thienyl | H | 2 |
| H | H | CH$_3$ | 5-Chloro-2-thienyl | H | 2 |
| H | H | H | 2-Methyl-5-nitro-1-imidazolyl | H | 2 |
| H | H | CH$_3$ | 2-Methyl-5-nitro-1-imidazolyl | H | 2 |
| H | H | H | 2-Methyl-5-nitro-1-imidazolyl | H | 3 |
| H | H | CH$_3$ | 2-Methyl-5-nitro-1-imidazolyl | H | 3 |
| H | H | H | 5-Nitro-1-imidazolyl | H | 2 |
| H | H | CH$_3$ | 5-Nitro-1-imidazolyl | H | 2 |
| H | H | H | 5-Nitro-1-imidazolyl | H | 3 |
| H | H | CH$_3$ | 5-Nitro-1-imidazolyl | H | 3 |

TABLE 4

Compounds of the formula I (see attached formula sheet I) where X = CH, R3 = SO$_2$CH$_3$, R6 = C$_m$H$_{2m}$-R6a, n = 0 and the following further substituent definitions:

| R1 | R2 | R5 | R6a | R7 | m |
|---|---|---|---|---|---|
| H | H | H | 2-Furyl | H | 1 |
| H | H | H | 2-Thienyl | H | 1 |
| H | H | H | 3-Thienyl | H | 1 |
| H | H | H | 5-Dimethylaminomethyl-2-furyl | H | 1 |
| H | H | H | 5-Piperidinomethyl-2-furyl | H | 1 |
| H | H | H | 5-Dimethylaminomethyl-2-thienyl | H | 1 |
| H | H | H | 2-Amino-4-thiazolyl | H | 1 |
| H | H | H | 2-Dimethylaminomethyl-4-thiazolyl | H | 1 |
| H | H | H | 2-Guanidino-4-thiazolyl | H | 1 |
| H | H | H | 2-Formylamino-4-thiazolyl | H | 1 |
| H | H | H | 4-Methyl-5-thiazolyl | H | 1 |
| H | H | H | 2-Methyl-4-imidazolyl | H | 1 |
| H | H | H | 5-Methyl-4-imidazolyl | H | 1 |
| H | H | H | 5-Amino-1,2,4-thiadiazol-3-yl | H | 1 |
| H | H | CH$_3$ | 2-Furyl | H | 1 |
| H | H | CH$_3$ | 2-Thienyl | H | 1 |
| H | H | CH$_3$ | 3-Thienyl | H | 1 |
| H | H | CH$_3$ | 5-Dimethylaminomethyl-2-furyl | H | 1 |
| H | H | CH$_3$ | 5-Piperidinomethyl-2-furyl | H | 1 |
| H | H | CH$_3$ | 5-Dimethylaminomethyl-2-thienyl | H | 1 |
| H | H | CH$_3$ | 2-Amino-4-thiazolyl | H | 1 |
| H | H | CH$_3$ | 2-Dimethylaminomethyl-4-thiazolyl | H | 1 |
| H | H | CH$_3$ | 2-Guanidino-4-thiazolyl | H | 1 |
| H | H | CH$_3$ | 2-Formylamino-4-thiazolyl | H | 1 |
| H | H | CH$_3$ | 4-Methyl-5-thiazolyl | H | 1 |
| H | H | CH$_3$ | 2-Methyl-4-imidazolyl | H | 1 |
| H | H | CH$_3$ | 5-Methyl-4-imidazolyl | H | 1 |
| H | H | CH$_3$ | 5-Amino-1,2,4-thiadiazol-3-yl | H | 1 |
| H | H | H | 2-Furyl | H | 2 |
| H | H | H | 2-Thienyl | H | 2 |
| H | H | H | 3-Thienyl | H | 2 |
| H | H | H | 5-Dimethylaminomethyl-2-furyl | H | 2 |
| H | H | H | 5-Piperidinomethyl-2-furyl | H | 2 |
| H | H | H | 5-Dimethylaminomethyl-2-thienyl | H | 2 |
| H | H | H | 2-Amino-4-thiazolyl | H | 2 |
| H | H | H | 2-Dimethylaminomethyl-4-thiazolyl | H | 2 |
| H | H | H | 2-Guanidino-4-thiazolyl | H | 2 |
| H | H | H | 2-Formylamino-4-thiazolyl | H | 2 |
| H | H | H | 4-Methyl-5-thiazolyl | H | 2 |
| H | H | H | 2-Methyl-4-imidazolyl | H | 2 |
| H | H | H | 5-Methyl-4-imidazolyl | H | 2 |
| H | H | H | 5-Amino-1,2,4-thiadiazol-3-yl | H | 2 |
| H | H | CH$_3$ | 2-Furyl | H | 2 |
| H | H | CH$_3$ | 2-Thienyl | H | 2 |
| H | H | CH$_3$ | 3-Thienyl | H | 2 |
| H | H | CH$_3$ | 5-Dimethylaminomethyl-2-furyl | H | 2 |
| H | H | CH$_3$ | 5-Piperidinomethyl-2-furyl | H | 2 |
| H | H | CH$_3$ | 5-Dimethylaminomethyl-2-thienyl | H | 2 |
| H | H | CH$_3$ | 2-Amino-4-thiazolyl | H | 2 |
| H | H | CH$_3$ | 2-Dimethylaminomethyl-4-thiazolyl | H | 2 |
| H | H | CH$_3$ | 2-Guanidino-4-thiazolyl | H | 2 |
| H | H | CH$_3$ | 2-Formylamino-4-thiazolyl | H | 2 |
| H | H | CH$_3$ | 4-Methyl-5-thiazolyl | H | 2 |
| H | H | CH$_3$ | 2-Methyl-4-imidazolyl | H | 2 |
| H | H | CH$_3$ | 5-Methyl-4-imidazolyl | H | 2 |
| H | H | CH$_3$ | 5-Amino-1,2,4-thiadiazol-3-yl | H | 2 |
| H | H | H | 5-Chloro-2-thienyl | H | 1 |
| H | H | CH$_3$ | 5-Chloro-2-thienyl | H | 1 |
| H | H | H | 5-Chloro-2-thienyl | H | 2 |
| H | H | CH$_3$ | 5-Chloro-2-thienyl | H | 2 |
| H | H | H | 2-Methyl-5-nitro-1-imidazolyl | H | 2 |
| H | H | CH$_3$ | 2-Methyl-5-nitro-1-imidazolyl | H | 2 |
| H | H | H | 2-Methyl-5-nitro-1-imidazolyl | H | 3 |
| H | H | CH$_3$ | 2-Methyl-5-nitro-1-imidazolyl | H | 3 |
| H | H | H | 5-Nitro-1-imidazolyl | H | 2 |
| H | H | CH$_3$ | 5-Nitro-1-imidazolyl | H | 2 |
| H | H | H | 5-Nitro-1-imidazolyl | H | 3 |
| H | H | CH$_3$ | 5-Nitro-1-imidazolyl | H | 3 |

TABLE 5

Compounds of the formula I (see attached forrmula sheet I)

where X = CH, R3 = CH$_2$CH$_2$COOCH$_3$, R6 = C$_m$H$_{2m}$-R6a,
n = 0 and the following further substituent definitions:

| R1 | R2 | R5 | R6a | R7 | m |
|---|---|---|---|---|---|
| H | H | H | 2-Furyl | H | 1 |
| H | H | H | 2-Thienyl | H | 1 |
| H | H | H | 3-Thienyl | H | 1 |
| H | H | H | 5-Dimethylaminomethyl-2-furyl | H | 1 |
| H | H | H | 5-Piperidinomethyl-2-furyl | H | 1 |
| H | H | H | 5-Dimethylaminomethyl-2-thienyl | H | 1 |
| H | H | H | 2-Amino-4-thiazolyl | H | 1 |
| H | H | H | 2-Dimethylaminomethyl-4-thiazolyl | H | 1 |
| H | H | H | 2-Guanidino-4-thiazolyl | H | 1 |
| H | H | H | 2-Formylamino-4-thiazolyl | H | 1 |
| H | H | H | 4-Methyl-5-thiazolyl | H | 1 |
| H | H | H | 2-Methyl-4-imidazolyl | H | 1 |
| H | H | H | 5-Methyl-4-imidazolyl | H | 1 |
| H | H | H | 5-Amino-1,2,4-thiadiazol-3-yl | H | 1 |
| H | H | CH$_3$ | 2-Furyl | H | 1 |
| H | H | CH$_3$ | 2-Thienyl | H | 1 |
| H | H | CH$_3$ | 3-Thienyl | H | 1 |
| H | H | CH$_3$ | 5-Dimethylaminomethyl-2-furyl | H | 1 |
| H | H | CH$_3$ | 5-Piperidinomethyl-2-furyl | H | 1 |
| H | H | CH$_3$ | 5-Dimethylaminomethyl-2-thienyl | H | 1 |
| H | H | CH$_3$ | 2-Amino-4-thiazolyl | H | 1 |
| H | H | CH$_3$ | 2-Dimethylaminomethyl-4-thiazolyl | H | 1 |
| H | H | CH$_3$ | 2-Guanidino-4-thiazolyl | H | 1 |
| H | H | CH$_3$ | 2-Formylamino-4-thiazolyl | H | 1 |
| H | H | CH$_3$ | 4-Methyl-5-thiazolyl | H | 1 |
| H | H | CH$_3$ | 2-Methyl-4-imidazolyl | H | 1 |
| H | H | CH$_3$ | 5-Methyl-4-imidazolyl | H | 1 |
| H | H | CH$_3$ | 5-Amino-1,2,4-thiadiazol-3-yl | H | 1 |
| H | H | H | 2-Furyl | H | 2 |
| H | H | H | 2-Thienyl | H | 2 |
| H | H | H | 3-Thienyl | H | 2 |
| H | H | H | 5-Dimethylaminomethyl-2-furyl | H | 2 |
| H | H | H | 5-Piperidinomethyl-2-furyl | H | 2 |
| H | H | H | 5-Dimethylaminomethyl-2-thienyl | H | 2 |
| H | H | H | 2-Amino-4-thiazolyl | H | 2 |
| H | H | H | 2-Dimethylaminomethyl-4-thiazolyl | H | 2 |
| H | H | H | 2-Guanidino-4-thiazolyl | H | 2 |
| H | H | H | 2-Formylamino-4-thiazolyl | H | 2 |
| H | H | H | 4-Methyl-5-thiazolyl | H | 2 |
| H | H | H | 2-Methyl-4-imidazolyl | H | 2 |
| H | H | H | 5-Methyl-4-imidazolyl | H | 2 |
| H | H | H | 5-Amino-1,2,4-thiadiazol-3-yl | H | 2 |
| H | H | CH$_3$ | 2-Furyl | H | 2 |
| H | H | CH$_3$ | 2-Thienyl | H | 2 |
| H | H | CH$_3$ | 3-Thienyl | H | 2 |
| H | H | CH$_3$ | 5-Dimethylaminomethyl-2-furyl | H | 2 |
| H | H | CH$_3$ | 5-Piperidinomethyl-2-furyl | H | 2 |
| H | H | CH$_3$ | 5-Dimethylaminomethyl-2-thienyl | H | 2 |
| H | H | CH$_3$ | 2-Amino-4-thiazolyl | H | 2 |
| H | H | CH$_3$ | 2-Dimethylaminomethyl-4-thiazolyl | H | 2 |
| H | H | CH$_3$ | 2-Guanidino-4-thiazolyl | H | 2 |
| H | H | CH$_3$ | 2-Formylamino-4-thiazolyl | H | 2 |
| H | H | CH$_3$ | 4-Methyl-5-thiazolyl | H | 2 |
| H | H | CH$_3$ | 2-Methyl-4-imidazolyl | H | 2 |
| H | H | CH$_3$ | 5-Methyl-4-imidazolyl | H | 2 |
| H | H | CH$_3$ | 5-Amino-1,2,4-thiadiazol-3-yl | H | 2 |
| H | H | H | 5-Chloro-2-thienyl | H | 1 |
| H | H | CH$_3$ | 5-Chloro-2-thienyl | H | 1 |
| H | H | H | 5-Chloro-2-thienyl | H | 2 |
| H | H | CH$_3$ | 5-Chloro-2-thienyl | H | 2 |
| H | H | H | 2-Methyl-5-nitro-1-imidazolyl | H | 2 |
| H | H | CH$_3$ | 2-Methyl-5-nitro-1-imidazolyl | H | 2 |
| H | H | H | 2-Methyl-5-nitro-1-imidazolyl | H | 3 |
| H | H | CH$_3$ | 2-Methyl-5-nitro-1-imidazolyl | H | 3 |
| H | H | H | 5-Nitro-1-imidazolyl | H | 2 |
| H | H | CH$_3$ | 5-Nitro-1-imidazolyl | H | 2 |
| H | H | H | 5-Nitro-1-imidazolyl | H | 3 |
| H | H | CH$_3$ | 5-Nitro-1-imidazolyl | H | 3 |

TABLE 6

Compounds of the formula I (see attached formula sheet I) where X = CH, R3 = CO—N(CH$_3$)$_2$, R6 = C$_m$H$_{2m}$-R6a, n = 0 and the following further substituent definitions:

| R1 | R2 | R5 | R6a | R7 | m |
|---|---|---|---|---|---|
| H | H | H | 2-Furyl | H | 1 |
| H | H | H | 2-Thienyl | H | 1 |
| H | H | H | 3-Thienyl | H | 1 |
| H | H | H | 5-Dimethylaminomethyl-2-furyl | H | 1 |
| H | H | H | 5-Piperidinomethyl-2-furyl | H | 1 |
| H | H | H | 5-Dimethylaminomethyl-2-thienyl | H | 1 |
| H | H | H | 2-Amino-4-thiazolyl | H | 1 |
| H | H | H | 2-Dimethylaminomethyl-4-thiazolyl | H | 1 |
| H | H | H | 2-Guanidino-4-thiazolyl | H | 1 |
| H | H | H | 2-Formylamino-4-thiazolyl | H | 1 |
| H | H | H | 4-Methyl-5-thiazolyl | H | 1 |
| H | H | H | 2-Methyl-4-imidazolyl | H | 1 |
| H | H | H | 5-Methyl-4-imidazolyl | H | 1 |
| H | H | H | 5-Amino-1,2,4-thiadiazol-3-yl | H | 1 |
| H | H | CH$_3$ | 2-Furyl | H | 1 |
| H | H | CH$_3$ | 2-Thienyl | H | 1 |
| H | H | CH$_3$ | 3-Thienyl | H | 1 |
| H | H | CH$_3$ | 5-Dimethylaminomethyl-2-furyl | H | 1 |
| H | H | CH$_3$ | 5-Piperidinomethyl-2-furyl | H | 1 |
| H | H | CH$_3$ | 5-Dimethylaminomethyl-2-thienyl | H | 1 |
| H | H | CH$_3$ | 2-Amino-4-thiazolyl | H | 1 |
| H | H | CH$_3$ | 2-Dimethylaminomethyl-4-thiazolyl | H | 1 |
| H | H | CH$_3$ | 2-Guanidino-4-thiazolyl | H | 1 |
| H | H | CH$_3$ | 2-Formylamino-4-thiazolyl | H | 1 |
| H | H | CH$_3$ | 4-Methyl-5-thiazolyl | H | 1 |
| H | H | CH$_3$ | 2-Methyl-4-imidazolyl | H | 1 |
| H | H | CH$_3$ | 5-Methyl-4-imidazolyl | H | 1 |
| H | H | CH$_3$ | 5-Amino-1,2,4-thiadiazol-3-yl | H | 1 |
| H | H | H | 2-Furyl | H | 2 |
| H | H | H | 3-Thienyl | H | 2 |
| H | H | H | 5-Dimethylaminomethyl-2-furyl | H | 2 |
| H | H | H | 5-Piperidinomethyl-2-furyl | H | 2 |
| H | H | H | 5-Dimethylaminomethyl-2-thienyl | H | 2 |
| H | H | H | 2-Amino-4-thiazolyl | H | 2 |
| H | H | H | 2-Dimethylaminomethyl-4-thiazolyl | H | 2 |
| H | H | H | 2-Guanidino-4-thiazolyl | H | 2 |
| H | H | H | 2-Formylamino-4-thiazolyl | H | 2 |
| H | H | H | 4-Methyl-5-thiazolyl | H | 2 |
| H | H | H | 2-Methyl-4-imidazolyl | H | 2 |
| H | H | H | 5-Methyl-4-imidazolyl | H | 2 |
| H | H | H | 5-Amino-1,2,4-thiadiazol-3-yl | H | 2 |
| H | H | CH$_3$ | 2-Furyl | H | 2 |
| H | H | CH$_3$ | 2-Thienyl | H | 2 |
| H | H | CH$_3$ | 3-Thienyl | H | 2 |
| H | H | CH$_3$ | 5-Dimethylaminomethyl-2-furyl | H | 2 |
| H | H | CH$_3$ | 5-Piperidinomethyl-2-furyl | H | 2 |
| H | H | CH$_3$ | 5-Dimethylaminomethyl-2-thienyl | H | 2 |
| H | H | CH$_3$ | 2-Amino-4-thiazolyl | H | 2 |
| H | H | CH$_3$ | 2-Dimethylaminomethyl-4-thiazolyl | H | 2 |
| H | H | CH$_3$ | 2-Guanidino-4-thiazolyl | H | 2 |
| H | H | CH$_3$ | 2-Formylamino-4-thiazolyl | H | 2 |
| H | H | CH$_3$ | 4-Methyl-5-thiazolyl | H | 2 |
| H | H | CH$_3$ | 2-Methyl-4-imidazolyl | H | 2 |
| H | H | CH$_3$ | 5-Methyl-4-imidazolyl | H | 2 |
| H | H | CH$_3$ | 5-Amino-1,2,4-thiadiazol-3-yl | H | 2 |
| H | H | H | 5-Chloro-2-thienyl | H | 1 |
| H | H | CH$_3$ | 5-Chloro-2-thienyl | H | 1 |
| H | H | H | 5-Chloro-2-thienyl | H | 2 |
| H | H | CH$_3$ | 5-Chloro-2-thienyl | H | 2 |
| H | H | H | 2-Methyl-5-nitro-1-imidazolyl | H | 2 |
| H | H | CH$_3$ | 2-Methyl-5-nitro-1-imidazolyl | H | 2 |
| H | H | H | 2-Methyl-5-nitro-1-imidazolyl | H | 3 |
| H | H | CH$_3$ | 2-Methyl-5-nitro-1-imidazolyl | H | 3 |
| H | H | H | 5-Nitro-1-imidazolyl | H | 2 |
| H | H | CH$_3$ | 5-Nitro-1-imidazolyl | H | 2 |
| H | H | H | 5-Nitro-1-imidazolyl | H | 3 |
| H | H | CH$_3$ | 5-Nitro-1-imidazolyl | H | 3 | and the salts of the compounds mentioned in the above tables.

The invention also relates to a process for the preparation of the compounds of the formula I and their salts.

The process comprises:

a) Reacting mercaptobenzimidazoles of the formula II (see attached formula sheet I), in which R1, R2, R3 and X have the abovementioned meanings, with picoline derivatives III (see attached formula sheet I), in which R5, R6 and R7 have the abovementioned meanings and A is a suitable leaving group, or b) Reacting benzimidazoles of the formula IV (see attached formula sheet II), in which R1, R2, R3 and X have the abovementioned meanings and A is a suitable leaving group, with pyridines of the formula V (see attached formula sheet II), in which R5, R6 and R7 have the abovementioned meanings, or c) Reacting compounds of the formula VI (see attached formula sheet II), in which R1, R2, R3, R5, F7, X and n have the abovementioned meanings and Hal is a halogen atom, with thiols R6SH, and (if compounds of the formula I where n=1 are the desired end products) subsequently oxidizing the resulting 2-benzimidazolyl-2-pyridylmethyl sulfides of the formula I where n=0, and/or, if desired, subsequently converting resulting compounds into the salts, and/or, if desired, subsequently converting resulting salts into the free compounds.

The compounds II to VI can be employed as such or, where appropriate, in the form of their salts in the reaction described above.

The reaction of II with III is carried out in suitable solvents, preferably polar protic or aprotic solvents (such as methanol, isopropanol, dimethyl sulfoxide, acetone, dimethylformamide or acetonitrile), with the addition or exclusion of water. It is carried out, for example, in the presence of a proton acceptor. Suitable proton acceptors are alkali metal hydroxides, such as sodium hydroxide, alkali metal carbonates, such as potassium carbonate, or tertiary amines, such as pyridine, triethylamine or ethyldiisopropylamine. Alternatively, the reaction can also be carried out without a proton acceptor, in which case—depending on the nature of the starting compounds—if appropriate, the acid addition salts can initially be separated off in a particularly pure form. The reaction temperature can be between 0° and 150° C., temperatures between 20° C. and 80° C. being preferred in the presence of proton acceptors and between 60° C. and 120° C.—in particular the boiling point of the solvents used—being preferred without proton acceptors. The reaction times are between 0.5 and 12 hours.

The reaction of the compounds IV with the compounds V is carried out in principle in a manner analogous to the reaction of the compounds II with the compounds III.

The reaction of a radical of one of the compounds VI with the thiols R6SH is carried out in a manner known per se, such as is known to the expert for the preparation of sulfides from thiols and halogenated aromatics. The halogen atom Hal is preferably a chlorine atom.

The oxidation of the sulfides (compounds of the formula I where n=0) to the sulfoxides (compounds of the formula I where n=1) is carried out under the conditions familiar to the expert for the oxidation of sulfides to sulfoxides [in this context cf., for example, J. Drabowicz and M. Mikolajczyk, Organic preparations and procedures int. 14(1–2), 45–89 (1982) or E. Block in S. Patai, The Chemistry of Functional Groups, Supplement E. Part 1, pages 539–608, John Wiley and Sons (Interscience Publication), 1980]. Possible oxidizing agents are all the reagents usually used for oxidation of sulfides to sulfoxides, in particular peroxy acids, such as, for example, peroxyacetic acid, trifluoroperoxyacetic acid, 3,5-dinitroperoxybenzoic acid, peroxymaleic acid, magnesium monoperoxyphthlate or, preferably, m-chloroperoxybenzoic acid.

The reaction temperature is between −70° C. and the boiling point of the solvent used (depending on the reactivity of the oxidizing agent and the degree of dilution), but preferably between −30° and +20° C. Oxidation with halogens or with hypohalites (for example with aqueous sodium hypochlorite solution), which is expediently carried out at temperatures between 0° and 50° C., has also proved advantageous. The reaction is expediently carried out in inert solvents, for example aromatic or chlorinated hydrocarbons, such as benzene, toluene, methylene chloride or chloroform, preferably in esters or ethers, such as ethyl acetate, isopropyl acetate or dioxane, or in alcohols, preferably isopropanol.

The sulfoxides according to the invention are optically active compounds. Further chirality centers can also be present in the molecule, depending on the nature of the substituents. The invention therefore relates both to the enantiomers and diastereomers and to their mixtures and racemates. The enatiomers can be separated in a manner known per se (for example by preparation and separation of corresponding diastereoisomeric compounds; cf., for example, WO92/08716).

The compounds II are known, for example, from WO86/02646, EP 134 400 or EP 127 763. The compounds III can be prepared, for example, as described in the following examples.

The thiols R6SH required for the preparation of III and V can be prepared, for example, from the corresponding halogen compounds analogously to J. Med. Chem. 14 (1971) 349.

The compounds IV, V and VI are likewise known, or they can be prepared by processes known per se from known starting compounds in an analogous manner. Thus, for example, compounds of the formula VI are obtained by reaction of compounds of the formula II with 4-halogenopyridines which correspond to compounds of the formula III.

The following examples serve to illustrate the preparation of the compounds according to the invention in more detail. In particular, the examples also serve to describe the preparation of selected starting compounds by way of example. Further compounds of the formula I and further starting compounds, the preparation of which is not described explicitly, can likewise be prepared in an analogous manner or in a manner with which the expert is familiar, using the customary process techniques. The abbreviation RT stands for room temperature, h stands for hour(s), m.p. for melting point and decomp. for decomposition.

EXAMPLES

End Products 1. 2-{[[4-(2-Furylmethylthio)-3-methyl-2-pyridinyl]methyl]thio}-1H-imidazo-[2,3-b]-pyridine 2-Chloromethyl-4-(2-furylmethylthio)-3-methyl-pyridine hydrochloride are stirred together with 2-mercapto-1H-imidazo-[2,3-b]-pyridine (1.05 equivalents) and sodium hydroxide solution (2.2 equivalents) in ethanol/water (1:1) at 60° C. for 20 h, the ethanol is then distilled off, the mixture is extracted with ethylacetate and the product is chromatographed over silica gel (methylene chloride/methanol 20:1 to 3:1). After crystallization from methanol/toluene, the title compound is obtained; m.p. 184–186° C.; colorless crystals; yield: 71% of theory.

2. 2-{[[3-Methyl-4-[2-(4-methyl-5-thiazolyl)-ethylthio]-2-pyridinyl]methyl]thio}-1H-imidazo-[2,3-b]-pyridine By the procedure described in Example 1, the title compound is obtained by reaction with 2-chloromethyl-3-methyl-4-[2-(4-methyl-5-thiazolyl)-ethylthio]-pyridine hydrochloride; m.p. 155° C. (decomp.); yield: 38% of theory.

3. 2-{[[4-(2-furylmethylthio)-3-methoxy-2-pyridinyl]methyl]thio}-1H-imidazo-[2,3-b]-pyridine By the procedure described in Example 1, the title compound is obtained with 2-chloromethyl-4-[2-furylmethylthio)-3-methoxy-pyridine hydrochloride; gray powder; m.p. 170–172° C.; yield: 69% of theory.

4. 1-(2-Dimethylaminoethyl)-2-{[[4-(2-furylmethylthio)-3-methyl-2-pyridinyl]methyl]-thio}-benzimidazole 2-{[[4-(2-Furylmethylthio)-3-methyl-2-pyridinyl]methyl]thio}-1H-benzimidazole is stirred with 2-dimethylamino-ethyl chloride hydrochloride (1.5 equivalents), potassium carbonate (5 equivalents) and potassium iodide (0.05 equivalents) in acetonitrile at 100° C. for 24 h, the mixture is filtered, the filtrate is concentrated on a rotary evaporator, water is added to the residue and the mixture is extracted with methylene chloride. The combined organic phases are washed with water, dried and concentrated. The residue is crystallized from methylene chloride/diisopropyl ether. The title compound is obtained as a colorless powder; m.p. 87–89° C.; yield: 74% of theory.

5. 1-(2-Ethoxycarbonyl-ethyl)-2-{[[4-(2-furylmethylthio-3-methyl-2-pyridinyl]]methyl]thio}-benzimidazole By the procedure described in Example 4, the title compound is obtained by reaction with ethyl 3-bromopropionate; m.p. 84–85° C.; yield: 84% of theory.

6. 2-{[[4-(2-furylmethylthio)-3-methyl-2-pyridinyl]methyl]thio}-1H-benzimidazole-1-(2-carboxylato-ethyl)-sodium 1-(2-Ethoxycarbonyl-ethyl)-2-{[[4-furyl-methylthio)-3-methyl-2-pyridinyl]methyl]thio}-1H-benzimidazole (1.0 g) is stirred in tetrahydrofuran (20 ml) with 2.2 ml of 1N sodium hydroxide solution at 25° C. for 4 days. The solid which has precipitated out is filtered off, washed with tetrahydrofuran and dried in vacuo. The title compound is obtained; m.p. 143–145° C.; yield: 77% of theory.

7. 1-Acetyl-2-{[[4-(2-furylmethylthio)-3-methyl-2-pyridinyl]methyl]thio}benzimidazole 2-{[[4-(2-Furylmethylthio)-3-methyl-2-pyridinyl]methyl]thio}-1H-benzimidazole (5.0 mmol) is suspended in anhydrous methylene chloride (50 ml), triethylamine (11 mmol and acetyl chloride (8 mmol) are added and the mixture is stirred at 20° C. for 20 h. The clear reaction solution is washed with sodium bicarbonate solution and water, dried over magnesium sulfate and concentrated and the residue is crystallized by addition of diisopropyl ether. The title compound is obtained as a colorless powder; m.p. 168–169° C. (decomp.); yield: 97% of theory.

8. 1-Acryloyl-2-{[[4-(2-furylmethylthio)-3-methyl-2-pyridinyl]methyl]thio}benzimidazole By the procedure described in Example 7, the title compound is obtained by reaction with 3-chloropropionyl chloride; m.p. 133–135° C. (decomp.); yield: 87% of theory.

9. 1-n-Butyroyl-2-{[[4-(2-furylmethylthio)-3-methyl-2-pyridinyl]methyl]thio}benzimidazole By the procedure described in Example 7, the title compound is obtained with 4-chlorobutyryl chloride; m.p. 168–170° C.; yield: 96% of theory.

10. 2-{[[4-(2-Furylmethylthio)-3-methyl-2-pyridinyl]methyl]thio}-1-methylsulfonyl-benzimidazole By the procedure described in Example 7, the title compound is obtained as a colorless powder with methanesulfonyl chloride; m.p. 163–164° C. (decomp.); yield: 94% of theory.

11. 2-{[[4-(2-Furylmethylthio)-3-methyl-2-pyridinyl] sulfinyl}-1H-imidazo[2,3-b]-pyridine 2-{[[4-(2-Furylmethylthio)-3-methyl-2-pyridinyl]-methyl]thio}-1H-imidazo[2,3-b]-pyridine (1.0 mmol) is dissolved in dioxane (10 ml). 2N sodium hydroxide solution (4.4 mmol) is added and sodium hypochlorite solution is added dropwise at 20° C. When the reaction is complete, sodium thiosulfate solution is added, the dioxane is distilled off, the pH is brought to 8, the mixture is extracted with methylene chloride, the organic phases are dried over magnesium sulfate and concentrated and the residue is crystallized from diisopropyl ether. The title compound is obtained as a beige powder; m.p. 166–167° C. (decomp.); yield: 37% of theory.

12. 2-{3-Methyl-4-[3-(2-methyl-5-nitro-imidazol-1-yl)-propylthiol-pyridin-2-ylmethylthio}-1H-benzimidazole 1.1 g (3 mmol) of 2-[4-(3-chloro-propylthio-3-methyl-pyridin-2-ylmethyl]thio]-1H-benzimidazole, 0.38 g (3 mmol) of 2-methyl-5-nitroimidazole, 2.07 g (15 mmol) of potassium carbonate and one spatula-tip) of sodium iodide are suspended in 15 ml of acetonitrile and the suspension is boiled under reflux for 40 h. It is then concentrated on a rotary evaporator and the residue is taken up in 100 ml of water. The mixture is extracted 3 times with 50 ml of methylene chloride each time. The combined organic phases are washed 3 times with 20 ml of water. The organic phase is dried over magnesium sulfate, filtered and concentrated. The residue is chromatographed over silica gel with ethyl acetate/methanol/concentrated ammonia=89/10/1. From the crude product obtained in this manner, the title compound crystallizes on trituration with diisopropyl ether. m.p. 135° C. (decomp.); yield 0.37 g (27% of theory).

13. 2-{3-Methyl-4-[3-(2-methyl-5-nitro-imidazol-1-yl)-propylthiol-pyridin-2-ylmethanesulfinyl}-1H-benzimidazole 0.6 g (1.32 mmol) of 2-{3-Methyl-4-[3-(2-methyl-5-nitro-imidazol-1-yl)-propylthio]-pyridin-2-ylmethylthio}-1H-benzimidazole is dissolved in a mixture of 30 ml of dioxane and 0.9 ml (5.3 mmol) of 6N NaOH. 2 ml (4 mmol) of sodium hypochlorite solution (12% strength) are slowly added dropwise. When the reaction has ended, the dioxane is stripped off on a rotary evaporator. The aqueous solution which remains is neutralized with 2 M sodium dihydrogen phosphate solution and then extracted 4 times with methylene chloride. The combined organic phases are washed with water. The organic phase is dried over magnesium sulfate, filtered and concentrated. The residue is chromatographed over silica gel with ethyl acetate/methanol/concentrated ammonia=75/20/5. From the crude product obtained in this manner, the title compound crystallizes on trituration with diisopropyl ether. m.p. 64–66° C.; yield 0.35 g (56% of theory).

Starting Compounds

A. 2-Chloromethyl-4-(2-furylmethylthio)-3-methylpyridine hydrochloride a) 2,3-Dimethyl-4-(2-furylmethylthio)pyridine N-oxide 6 g (60% strength) of NaH are added in portions to 50 ml of dry dioxane, the mixture is stirred for 15 minutes, 11.7 g (0.11 mol) of 2-furylmethylmercaptan are metered in over a period of 20 minutes and the mixture is stirred again for 30 minutes until the evolution of gas has ended. A solution of 14.4 g (0.1 mol) of 4-chloro-2,3-dimethylpyridine N-oxide in 100 ml of dioxane is then added dropwise in the course of 20 minutes, and the reaction mixture is stirred at RT for 1 h, subsequently at 70° C. for 1 h and then at 100° C. for another 1 h. When the reaction has ended, the mixture is allowed to cool and is diluted with 500 ml of water and extracted 4 times with 300 ml of ethyl acetate each time. The combined organic phases are washed with water, dried over magnesium sulfate and concentrated and the residue is crystallized by addition of diisopropyl ether. 18.8 g (80% of theory) of 2,3-dimethyl-4-(2-furylmethylthio)-pyridine N-oxide of m.p. 111–112° C. are obtained.

b) 2-Acetoxymethyl-4-(2-furylmethylthio)-3-methylpyridine 18.0 g (0.77 mol) of the product obtained under a) are heated (100° C.) and stirred for 2 h in 100 ml of acetic anhydride. After concentration in vacuo, the brown, oily residue is distilled in a bulb tube distillation apparatus. 17.0 g of 2-acetoxymethyl-4-(2-furylmethylthio)-3-methylpyridine, which is further reacted directly, are obtained.

c) 4-(2-Furylmethylthio)-2-hydroxymethyl-3-methylpyridine

The product from b) (17.0 g) is heated at the reflux temperature in 100 ml of 2 N sodium hydroxide solution and 100 ml of isopropanol for 2 h, while stirring, the isopropanol is distilled off and the residue is extracted 3 times with 100 ml of methylene chloride each time. The combined organic phases are washed with water, dried over potassium carbonate and concentrated in vacuo and the residue is crystallized from a little toluene. 13.4 g (93%) of 4-(2-furylmethylthio)-2-hydroxymethyl-3-methylpyridine are obtained as a cream-colored solid of m.p. 60–62° C.

d) 2-Chloromethyl-4-(2-furylmethylthio)-3-methylpyridine hydrochloride 10.0 g (0.042 mol) of 4-(2-furylmethylthio)-2-hydroxymethyl-3-methylpyridine are dissolved in methylene chloride (100 ml), 1.2 equivalents of thionyl chloride are added dropwise at RT and the mixture is stirred at RT for 20 h. It is concentrated completely and the title compound is obtained as an oily residue, which gradually crystallizes and, if desired, can also be used as a solution in ethanol directly for reaction with substituted 2-mercaptobenzimidazoles. For purification, the residue is recrystallized from hot isopropanol with the addition of active charcoal. 9.0 g (74% of theory) of the title compound are obtained as colorless crystals of m.p. 159–161° C. (decomp.).

B) 2-Chloromethyl-3-methyl-4-[2-(4-methyl-5-thiazolyl)-ethylthiopyridine hydrochloride a) 2,3-Dimethyl-4-[2-(4-methyl-5-thiazolyl)-ethylthio]-pyridine N-oxide By the procedure described in Example Aa), 2,3-dimethyl-4-[2-(4-methyl-5-thiazolyl)-ethylthio]-pyridine N-oxide is obtained by reaction of 4-chloro-2,3-dimethylpyridine N-oxide with 5-(2-mercaptoethyl)-4-methylthiazole in the presence of sodium hydride; m.p.: 135–137° C. (yield: 79%).

b) 2-Acetoxymethyl-3-methyl-4-[2-(4-methyl-5-thiazolyl)-ethylthio]pyridine

By the procedure described in Example Ab), 2-acetoxymethyl-3-methyl-4-[2-(4-methyl-5-thiazolyl)-ethylthio]pyridine if obtained from product Ba) as a yellow oil, which is further reacted directly.

c) 2-Hydroxymethyl-3-methyl-4-[2-(4-methyl-5-thiazolyl)-ethylthio]pyridine

By the procedure described under Ac), the title compound, which can be further reacted directly as the crude product without crystallization, is obtained from product Bb).

d) 2-Chloromethyl-3-methyl-4-[2-(4-methyl-5-thiazolyl)-ethylthio]pyridine hydrochloride By the procedure described under Ad), the title compound, which is dissolved as the crude product in ethanol and further reacted directly, is obtained from product Bc).

C) 2-Chloromethyl-4-{[[(5-dimethylaminomethyl-2-furyl)methyl]thio}-3-methylpyridine hydrochloride a) 4-{[(5-Dimethylaminomethyl-2-furyl)methyl]thio}-2-hydroxymethyl-3-methyl]pyridine 1.5 g (6.4 mmol) of 5-(2-furylmethylthio)-2-hydroxymethyl-3-methyl-pyridine (prepared in accordance with Example Ac) are dissolved in 40 ml of acetonitrile, 1.5 g (8.0 mmol) of N,N-dimethyl-methyleneimmonium iodide are added and the mixture is stirred at 80° C. for 4 h. After the acetonitrile has been distilled off in vacuo, water (10 ml) is added to the residue, the pH is brought to 10 with sodium carbonate solution and the mixture is extracted with ethyl acetate (3×20 ml). The combined organic phases are washed with water, dried over potassium carbonate and concentrated and the residue is chromatographed over silica gel (methylene chloride/methanol/triethylamine 4/1/0.1). 1.06 g (57%) of the title compound are obtained as a yellow oil.

H NMR (CDCl$_3$): ppm 2.13 (s, 3H); 2.25 (s, 6H); 3.42 (s, 2H); 4.19 (s,2H); 4.68 (s, 2H); 6.10–6.19 (AB system, 2H); 7.15 (d, J=5.4 Hz, 1H); 8.23 (d, 1H).

After dissolving in diethyl ether, addition of ethered hydrochloric acid gives the title compound as a colorless, hygroscopic dihydrochloride. Decomp. from 90° C.

b) 2-Chloromethyl-4-{[(5-dimethylaminomethyl-2-furyl)methyl]thio}-3-methylpyridine dihydrochloride By the procedure described under Ad), the title compound is obtained as a crude product, which is dissolved in ethanol and further reacted directly, starting from the compound of Example Ca). Crystallization from isopropanol gives a crystalline, colorless dihydrochloride; m.p. from 185° C. (decomp.).

The hydrochlorides of the following compounds are obtained in an analogous manner—as described, for example, in Examples Aa) to Ad):
2-chloromethyl-3-methyl-4-(2-thienylmethylthio)-pyridine, 2-chloromethyl-3-methyl-4-(3-thienylmethylthio)-pyridine, 2-chloromethyl-3-methoxy-4-(2-thienylmethylthio)-pyridine, 2-chloromethyl-4-(2-thienylmethylthio)-pyridine, 2-chloromethyl-4-(2-furylmethylthio)-pyridine, 2-chloromethyl-4-[(3,4-dimethoxy)-2-pyridinyl-methylthio)]-3-methylpyridine and 2-chloromethyl-4-[2-pyridinyl-2-ethylthiol]-3-methylpyridine.

D) 2-Chloromethyl-4-{2-furylmethylthio)-3-methoxypyridine hydrochloride

By the procedure described in Aa) to Ac), the intermediate product 4-(2-furylmethylthio)-2-hydroxymethyl-3-methoxypyridine is obtained starting from 4-chloro-3-methoxy-2-methylpyridine N-oxide; m.p. 56–58° C. Chlorination with thionyl chloride by the procedure described in Example Ad) gives the title compound as a beige powder; m.p. 135° C. (decomp.).

Commercial Usefulness

The excellent activity of compounds of the formula I and their salts against Helicobacter bacteria enables them to be used in human medicine as active compounds for the treatment of diseases based on Helicobacter bacteria.

The invention therefore also relates to a process for the treatment of mammals, in particular humans, suffering from diseases based on Helicobacter bacteria. The process comprises administering to the sick individual a therapeutically active and pharmacologically tolerated amount of one or more compounds of the formula I and/or their pharmacologically tolerated salts.

The invention furthermore relates to the compounds of the formula I and their pharmacologically tolerated salts for use in the treatment of diseases based on Helicobacter bacteria.

The invention also relates to the use of compounds of the formula I and their pharmacologically tolerated salts for the preparation of medicaments which are employed for combating those diseases based on Helicobacter bacteria.

The invention also relates to medicaments for combating Helicobacter bacteria which comprise one or more compounds of the general formula I and/or their pharmacologically tolerated salts.

Of the Helicobacter strains against which the compounds of the formula I prove to be active, the strains Helicobacter pylori may be mentioned in particular.

The medicaments are prepared by processes known per se which are familiar to the expert. The pharmacologically active compounds of the formula I and their salts (=active compounds) are employed as medicaments either as such or, preferably, in combination with suitable pharmaceutical auxiliaries, for example in the form of tablets, coated tablets, capsules, emulsions, suspensions, gels or solutions, the active compound content advantageously being between 0.1 and 95%.

The expert is familiar with the auxiliaries which are suitable for the desired medicament formulations on the basis of his expert knowledge. In addition to solvents, gel-forming agents, tablet auxiliaries and other active compound carriers, it is possible to use, for example, antioxidants, dispersing agents, emulsifiers, defoamers, flavor correctants, preservatives, solubilizing agents, colorants or permeation promoters and complexing agents (for example cyclodextrins).

The active compounds can be administered, for example, parenterally (for example intravenously), or in particular orally.

In general, the active compounds are administered in human medicine in a daily dose of about 0.2 to 50, preferably 1 to 30 mg/kg of body weight, if appropriate in the form of several, preferably 2 to 6, individual doses to achieve the desired results.

In this connection, it is to be mentioned in particular, as an aspect essential to the invention, that the compounds of the formula I in which n is the number 0 prove to be active against Helicobacter bacteria even when administered in those doses which are below the doses which would have to be employed to achieve an inhibition of the secretion of gastric acid which is sufficient for therapeutic purposes.

Compounds of the formula I in which n is the number 1 also have—in addition to their activity against Helicobacter bacteria—a pronounced inhibitory action on secretion of gastric acid. These compounds can accordingly also be employed for treatment of those diseases which are based on an increased secretion of gastric acid.

The compounds according to the invention can also be administered in a fixed or free combination together with a substance which neutralizes gastric acid and/or inhibits secretion of gastric acid and/or with a substance which is suitable for controlling Helicobacter pylori in the conventional manner.

Examples which may be mentioned of substances which neutralize gastric acid are sodium bicarbonate or other antacids (such as aluminum hydroxide, magnesium aluminate or magaldrate). Examples which may be mentioned of substances which inhibit secretion of gastric acid are $H_2$-blockers (for example cimetidine or ranitidine), $H^+/K^+$-ATPase inhibitors (for example lansoprazole, omeprazole or, in particular, pantoprazole), and so-called peripheral anticholinergics (for example pirenzepine or telenzenpine).

Substances which are suitable for combating Helicobacter pylori in the conventional manner and which may be mentioned are, in particular, antimicrobially active substances, such as, for example, penicillin G, gentamycin, erythromycin, nitrofurazone, tinidazole, nitrofurantoin, furazolidone, metronidazole and, in particular, amoxycillin, or else bismuth salts, such as, for example, bismuth citrate.

Biological Studies

The compounds of the formula I were investigated in respect of their activity against Helicobacter pylori in accordance with the method described by Tomoyuki Iwahi et al. (Antimicrobial Agents and Chemotherapy, 1991, 490–496) using Columbia agar (Oxoid) with a growth period of 4 days. The approximate MIC 50 values listed in the following Table A (the numbers stated for the compounds coincide with the example numbers in the description) resulted in this test for the compounds investigated.

TABLE A

| Compound No. | Approximate MIC50 ($\mu$g/ml) |
|---|---|
| 1 | 0.1 |
| 7 | 0.5 |
| 8 | 0.1 |
| 9 | 0.1 |
| 10 | 0.5 |

FORMULA SHEET I

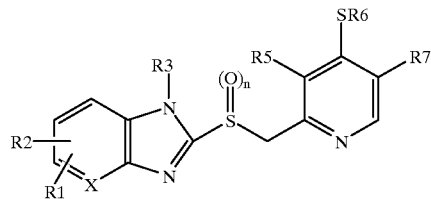

(I)

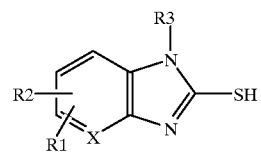

(II)

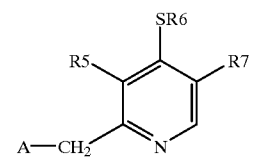

(III)

FORMULA SHEET II

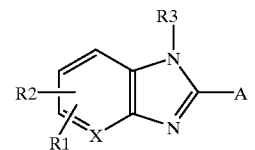

(IV)

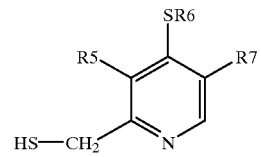

(V)

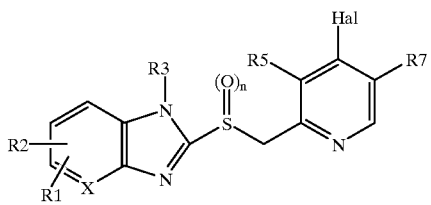

(VI)

What is claimed is:
1. A compound of formula I,

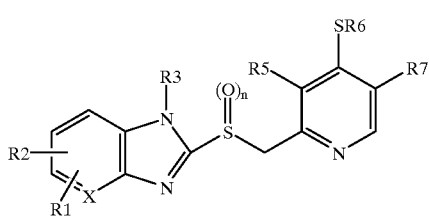

in which
R1 is hydrogen, 1–4C-alkoxy or halogen,
R2 is hydrogen or halogen,
R3 is hydrogen, R4-substituted 1–4C-alkyl, 1–4C-alkylcarbonyl, 2–4C-alkenylcarbonyl, halo-1–4C-alkylcarbonyl, N(R14)R15-1–4C-alkylcarbonyl, di-1–4C-alkylcarbamoyl or 1–4C-alkylsulfonyl,
R4 is carboxyl, 1–4C-alkoxycarbonyl or —N(R14)R15,
R5 is 1–4C-alkyl or 1–4C-alkoxy,
R6 is R8- and R9-substituted phenyl or the radical $C_mH_{2m}$—R6a,
R6a is a mono- or di-1–4C-alkylcarbamoyl or -thiocarbamoyl radical, an N-1–4C-alkyl-N'-cyanoamidino radical, a 1-N-1–4C-alkylamino-2-nitroethylene radical or an R8- and R9-substituted cyclic or bicyclic radical which is chosen from the group consisting of a radical of one of benzene, furan, thiophene, thiazole, isothiazole, imidazole, pyrazole, triazole, tetrazole, thiadiazole, oxadiazole, pyridine, pyrimidine, triazine, pyridone, benzimidazole and imidazopyridine,
R7 is hydrogen or 1–4C-alkyl,
R8 is hydrogen, 1–4C-alkyl, hydroxyl, nitro, guanidino, carboxyl, 1–4C-alkoxycarbonyl or R10-substituted 1–4C-alkyl,
R9 is hydrogen, 1–4C-alkyl, hydroxyl or fluorine,
R10 is hydroxyl, 1–4C-alkoxycarbonyl or —N(R11)R12, in which
R11 is 1–4C-alkyl and
R12 is 1–4C-alkyl, or in which
R11 and R12, together and including the nitrogen atom to which they are both bonded, are a piperidino or morpholino radical,
R14 is 1–4C-alkyl and
R15 is 1–4C-alkyl, or in which
R14 and R15, together and including the nitrogen atom to which they are both bonded, are a piperidino or morpholino radical,
n is the number 0 or 1,
m is a number from 1 to 4 and
X is CH,
or a salt thereof, excluding those compounds of formula I in which X is CH and at the same time
R1 is hydrogen or 1–4C-alkoxy,
R3 is hydrogen,
R6a is an R8- and R9-substituted cyclic radical which is chosen from the group consisting of benzene, furan, thiophene, thiazole, isothiazole, imidazole, pyrazole, triazole, tetrazole, thiadiazole, pyridine and pyrimidine,
R8 is hydrogen, 1–4C-alkyl, guanidino or R10-substituted 1–4C-alkyl,
R9 is hydrogen, 1–4C-alkyl or fluorine,
R10 is hydroxyl or —N(R11)R12 and
R2, R5, R6, R7, R11, R12, R13, R14, R15, n and m have one of the abovementioned meanings.
2. A compound of formula I as claimed in claim 1, in which
R1 is hydrogen, 1–4C-alkoxy or fluorine,
R2 is hydrogen or fluorine,
R3 is hydrogen, R4-substituted 1–4C-alkyl, N(R14)R15-1–4C-alkylcarbonyl, di-1–4C-alkylcarbamoyl or 1–4C-alkylsulfonyl,
R4 is 1–4C-alkoxycarbonyl or —N(R14)R15,
R5 is 1–4C-alkyl,
R6 is the radical $C_mH_{2m}$—R6a,
R6a is an R8- and R9-substituted cyclic radical which is chosen from the group consisting of a radical of one of benzene, furan, thiophene, thiazole, imidazole, triazole, tetrazole, pyridine and triazine,
R7 is hydrogen,
R8 is hydrogen, hydrogen or nitro,
R9 is hydrogen or 1–4C-alkyl,
R14 is 1–4C-alkyl and
R15 is 1–4C-alkyl, or in which
R14 and R15, together and including the nitrogen atom to which they are both bonded, are a piperidino or morpholino radical,
n is the number 0,
m is a number from 1 to 4 and
X is CH,
or a salt thereof, excluding those compounds of formula I in which X is CH and at the same time
R1 is hydrogen or 1–4C-alkoxy,
R3 is hydrogen,
R6a is an R8- and R9-substituted cyclic radical which is chosen from the group consisting of benzene, furan, thiophene, thiazole, imidazole, triazole, tetrazole and pyridine,
R8 is hydrogen,
R9 is hydrogen or 1–4C-alkyl,
R2, R5, R6, R7, R14, R15, n and m have one of the abovementioned meanings.
3. A compound of formula I as claimed in claim 1, in which
R1 is hydrogen,
R2 is hydrogen,
R3 is hydrogen,
R5 is 1–4C-alkyl,
R6 is the radical $C_mH_{2m}$—R6a, R6a is an R8- and R9-substituted cyclic radical which is chosen from the group consisting of a radical of one of benzene, furan, thiophene, thiazole, imidazole, triazole, tetrazole, pyridine and triazine, R7 is hydrogen, R8 is nitro, R9 is hydrogen or 1–4C-alkyl, n is the number 0, m is a number from 1 to 4 and X is CH, or a salt thereof.

4. A compound of formula I as claimed in claim 1, wherein R3 is R4-substituted 1–4C-alkyl, 1–4C-alkylcarbonyl, 2–4C-alkenylcarbonyl, halo-1–4C-alkylcarbonyl, N(R14)R15-1–4C-alkylcarbonyl, di-1–4C-alkylcarbamoyl or 1–4C-alkylsulfonyl.

5. A compound of a radical of one of the formula I as claimed in claim 1 in which R1 is hydrogen, 1–4C-alkoxy or halogen, R2 is hydrogen or halogen, R3 is hydrogen, R4-substituted 1–4C-alkyl, 1–4C-alkylcarbonyl, 2–4C-alkenylcarbonyl, halo-1–4C-alkylcarbonyl, N(R14)R15-1–4C-alkylcarbonyl, di-1–4C-alkylcarbamoyl or 1–4C-alkylsulfonyl, R4 is carboxyl, 1–4C-alkoxycarbonyl or —N(R14)15, R5 is 1–4C-alkyl or 1–4C-alkoxy, R6 is the radical $C_mH_{2m}$—R6a, R6a is an R8- and R9-substituted cyclic radical which is selected from the group consisting of benzene, furane, thiophene, thiazole, imidazole, triazole, tetrazole, pyridine and triazine, R7 is hydrogen, R8 is hydrogen, 1–4C-alkyl, hydroxyl, nitro, R9 is hydrogen, 1–4C-alkyl, hydroxyl or fluorine, R14 is 1–4C-alkyl and R15 is 1–4C-alkyl, or in which R14 and R15, together and including the nitrogen atom to which they are both bonded, are a piperidino or morpholino radical, n is the number 0 or 1, m is a number from 1 to 4 and X is CH, or a salt thereof, excluding those compounds of the formula I in which, at the same time, R1 is hydrogen or 1–4C-alkoxy, R3 is hydrogen, R6a is an R8- and R9-substituted cyclic radical which is selected from the group consisting of benzene, furan, thiophene, thiazole, imidazole, triazole, tetrazole and pyridine, R8 is hydrogen or 1–4C-alkyl, R9 is hydrogen, 1–4C-alkyl or fluorine, and R2, R5, R6, R7, R14, R15, n and m have one of the above-mentioned meanings.

6. A compound of claim 5, wherein R6 is that of the radical $C_mH_{2m}$—R6a, and the cyclic radical of R6a is that of furan.

7. A compound of claim 5, wherein R6 is that of the radical $C_mH_{2m}$—R6a, and the cyclic radical of R6a is that of imidazole.

8. A compound of claim 5, wherein R6 is that of the radical $C_mH_{2m}$—R6a, and the cyclic radical of R6a is that of thiazole.

9. A pharmaceutical composition comprising an effective amount of active ingredient for treating a disease based on Helicobacter bacteria and a suitable carrier therefor, and wherein the active ingredient is a compound of claim 1.

10. A method for compounding a medicament preparation by admixing an effective amount of active component for combating Helicobacter bacteria with a suitable carrier, wherein the active component is a compound of claim 1 or a pharmacologically tolerated salt thereof.

11. A method for treating an amerable disease based on Helicobacter bacteria which comprises administering an effective amount of a compound of claim 1 and/or a pharmacologically tolerated salt thereof to a subject afflicted with such disease.

* * * * *